United States Patent [19]
Huiku

[11] Patent Number: 6,147,351
[45] Date of Patent: Nov. 14, 2000

[54] ACCURATE MEASUREMENT FOR THE CONCENTRATION OF A GAS COMPONENT IN A GAS MIXTURE, WHEREIN OTHER COMPONENTS INFLUENCE THE CONCENTRATION ANALYSIS

[75] Inventor: Matti Huiku, Kaksoiskiventie, Finland

[73] Assignee: Instrumentarium Corp., Helsinki, Finland

[21] Appl. No.: 08/999,123

[22] Filed: Dec. 29, 1997

[30] Foreign Application Priority Data

Dec. 30, 1996 [FI] Finland .................................... 965250

[51] Int. Cl.$^7$ .................................................. G01N 21/61
[52] U.S. Cl. ........................... 250/343; 250/345; 356/437
[58] Field of Search .................................. 250/343, 345; 356/437

[56] References Cited

U.S. PATENT DOCUMENTS

| | | |
|---|---|---|
| 3,745,349 | 7/1973 | Liston . |
| 3,793,525 | 2/1974 | Burch et al. . |
| 3,878,107 | 4/1975 | Pembrook et al. . |
| 4,110,619 | 8/1978 | Zörner . |
| 4,423,739 | 1/1984 | Passaro et al. . |
| 4,849,636 | 7/1989 | Fertig, Sr. . |
| 5,036,198 | 7/1991 | Spaeth . |
| 5,055,688 | 10/1991 | Fabinski . |
| 5,486,699 | 1/1996 | Fabinski et al. . |
| 5,672,874 | 9/1997 | Fujii et al. .............................. 250/343 |
| 5,900,635 | 5/1999 | Weckstrom ............................. 250/343 |

FOREIGN PATENT DOCUMENTS

| | | |
|---|---|---|
| 405841 | 1/1991 | European Pat. Off. . |
| 94/24528 | 10/1994 | WIPO . |

OTHER PUBLICATIONS

*A Reliable, Accurate $CO_2$ Analyzer for Medical Use*, Rodney J. Solomon, Hewlett–Packard Journal, Sep. 1981, pp. 3–21.

*Air Broadened Linewidths, Intensities, and Spectral Line Shapes for $CO_2$ at 4.3 μm in the Region of the AMTS Instrument*, C. Cousin, R. Le Doucen, J.P. Houdeau, C. Boulet and A. Henry, Applied Optics, vol. 25, No. 14, Jul. 1986, pp. 2434–2439.

*Primary Examiner*—Constantine Hannaher
*Assistant Examiner*—Andrew Israel
*Attorney, Agent, or Firm*—Andrus, Sceales, Starke & Sawall, LLP

[57] ABSTRACT

A sensor device and a method for non-dispersive analysis of gas mixtures for determining the concentration of one gas component contained therein, whose absorbency may be influenced as a result of collision broadening by other components contained in a gas mixture (GC). The device includes: a measuring chamber (5), containing the gas mixture; a radiation source (4), emitting radiation (15) through the chamber; detector (10, 14, 16) for receiving radiation passed through the chamber; optical bandpass filters (9a–c) positioned between the detectors and the radiation source, the detectors being coupled with measuring ducts (1–3) or measuring cycles. An optical gas filter (11), contains said gas component or a mixture thereof and is located between the detector and the radiation source. From the first measuring duct is obtained a first signal (S1) and from the second measuring duct is obtained a second signal (S2) relating to radiation also passed through the optical gas filter. Prior to analyses, the amount of a gas component in the gas filter is set at its pressure and/or absorption length or alternatively the effective amount of gas component in its gas mixture either at its fixed concentration and/or at the pressure and/or absorption length (L2) of the mixture to have such a value that: the second signal (S2) and the first signal (S1) are linearly independent of each other and that the second signal and the first signal have a mutual relationship, wherein the variable quantities include at least a collision broadening and a gas component concentration and wherein the coefficients are experimentally determined prior to analyses for accurately determining the effect of a collision broadening.

35 Claims, 10 Drawing Sheets

FIG. 2A
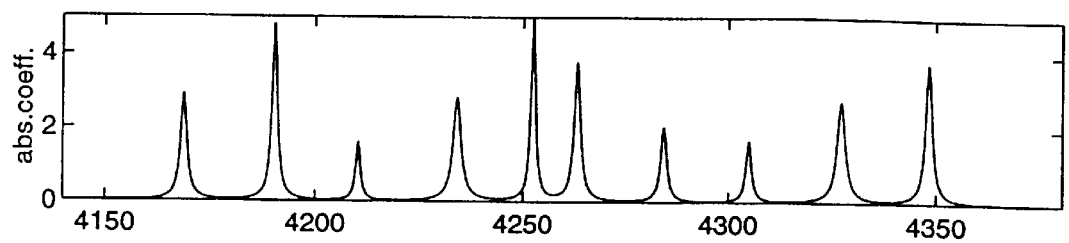
FIG. 2B
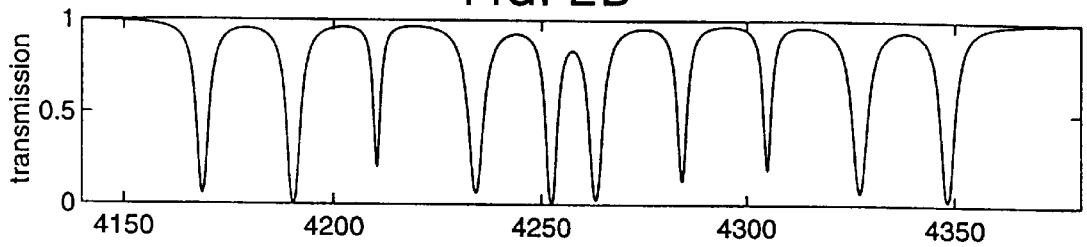
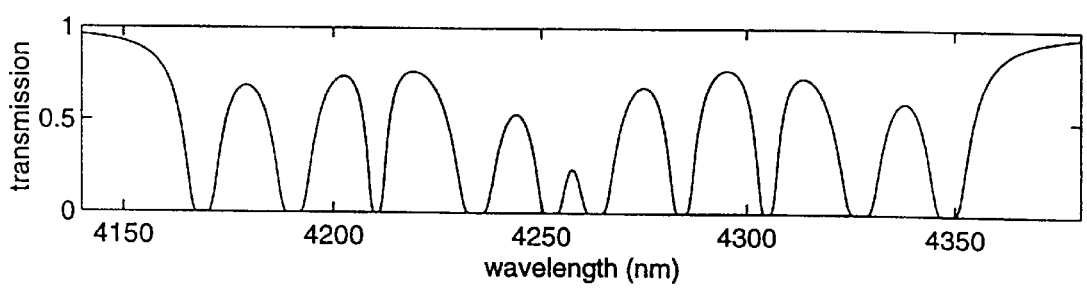
FIG. 2C

ACCURATE MEASUREMENT FOR THE CONCENTRATION OF A GAS COMPONENT IN A GAS MIXTURE, WHEREIN OTHER COMPONENTS INFLUENCE THE CONCENTRATION ANALYSIS

BACKGROUND OF THE INVENTION

The measurement of a gas concentration with infrared technology is generally implemented by means of a non-dispersive method, i.e. by measuring absorption through an appropriately selected bandpass filter. Thus, the measured attenuated radiation transmitted through the gas layer will be an integrated value of transmissions existing over various wavelengths of this band. This type of equipment is described for example in publications U.S. Pat. No. 3,745, 349 and HEWLETT PACKARD JOURNAL, September 1981, pp. 3–5: R. J. Solomon—"A Reliable, Accurate $CO_2$ Analyzer for Medical Use". The former publication discloses the use of two sources of infrared radiation emitting through a sample gas but, for example, an optical gas filter is used for removing characteristic wavelengths of an absorbing gas to be measured from the radiation coming from the first radiation source. The purpose is to establish a reference source, the radiation intensity produced thereby and detected by a detector not being influenced by a gas mixture to be examined. On the other hand, radiation from the second radiation source decays or attenuates strongly as a result of a gas mixture to be examined, whereby the proportional signal changes can be used for determining the concentration of a gas component to be studied. The method is also relatively effective for correcting the influence of contamination collecting in a measuring chamber and also other adverse effects, if the radiation sources are located on exactly the same optical path with respect to the detector. The latter publication deals in even more detail with problems associated with the determination of carbon dioxide, taking into account e.g. other gases interfering with a gas component to be examined. The publication discloses a solution by using a rotating disc, containing a variety of filters for obtaining a reference value. The measurement with infrared technology of a single gas component studied in the above-cited publications is in a way sensitized to a desired gas component by using special, i.e. primarily gas-filled, optical filters and often also gas-filled, e.g. pressure-detection based detectors, the filling gas in both of these consisting of a gas component to be studied. Based on the above, the available prior art will now be studied in a bit more detail.

There are several means for sensitizing the infrared measuring to a given gas component or for increasing the selectivity of measurement. When the infrared radiation is detected by using pneumatic, acoustic or capacitive gas-filled detectors, the measurement in a way sensitizes in itself to the very gas component used for filling the detector, since absorption is only within the absorption bands and absorption lines of this gas component, so that the absorption of radiation and, the gaining of a signal take place. If the question is about a wide-band detector, such as a so-called thermopile, a solid state detector or a thermistor, the sensitization of measurement is generally done by means of a narrow-band optical filter, having its passband preferably selected within the range over which the presently examined gas absorbs. Another option is to set upstream of the detector a gas-filled chamber, which eliminates radiation from the wavelengths of the absorption lines of this particular component, or it is possible to use both filters together. For example, US-publication 5,036,198 discloses a device combining the use of two rotating filter discs, one filter disc being provided with gas-filled, measurement-sensitizing, optical filters and the other with narrow-band optical band-pass filters appropriately complementing the former. The use of a wide variety of chambers and bandpass filters enables the concurrent measurement of several gas components. A complicated measuring system tailored as described above has also distinctive drawbacks. The measurement is only accurate for those gases which have been accounted for in the measuring process. Any unknown gas component absorbing within the transmission bands of optical filters ruins the measuring accuracy and, as a matter of fact, in order to cause error, the unknown gas component need not even be optically active since the gases influence each other also through collision broadening.

The publication U.S. Pat. No. 5,055,688 discloses a way of using gas-filled pneumatic detectors for sensitizing a measurement to a given or several gas components. The apparatus set forth in the publication employs two gas-filled detectors, each being further provided with two separate gas chambers. In addition, between the detectors is fitted a bandpass filter for ultimately sensitizing the detectors to various gas components, such as CO and $CO_2$. The bandpass filter is used for selecting such of the absorption bands of gases to be examined, which are spaced from each other and which provide an amplification stage connected to the detectors with a signal of the same magnitude, even though the mean gas concentrations subject to measuring were clearly different from each other. Generally, a problem encountered in measuring methods using gas-filled optical filters or detectors is that the detector, upstream of which lies an optical, strongly attenuating filter containing a gas component to be examined, has a signal which is very weak as compared to the signal of a so-called reference detector, which has no extra attenuation or absorption. This problem develops since the sensitization of a measurement to a predetermined gas requires a high selectivity or the major attenuation of radiation within the range of wavelengths over which the gas component to be measured absorbs. This difficulty is particularly pronounced in those measuring systems intended for measuring various isotopes of the same molecule, or in fact of a specified atom thereof. The US-publication 5,486,699 describes the measurement of various carbon isotopes by means of a solution, which involves quite a complicated chamber configuration and electronics for regulating in a special way the amplification and zero level of a signal produced by detectors.

The above-described prior art deals with such measuring systems, which employ gas-filled optical filters or detectors or optical bandpass filters in such a fashion that, in the vicinity of the absorption band of a gas to be analyzed, the influence of an absorbing, measurement-disturbing gas is eliminated or significantly reduced, or that the infrared measurement is accompanied by a reference measurement for recuding mechanical or e.g. contamination-induced influences, or that the measurement is performed on several different optically active gas components. The above-described prior art does not deal with changes occurring within a single absorption band of a gas molecule or, in practice, changes caused by collision broadening on the fine structure of an absorption band and an error resulting therefrom in the concentration analysis of a gas component.

The absorption spectrum of a gas in a molecular state consists normally of absorption bands produced by molecular vibrations and of a fine structure resulting from rotational transitions within the same. Thus, when measured with a sufficient resolution, the absorption spectrum of a gas consists of a large number of very narrow absorption lines. For example, carbon dioxide has a vibrational absorption band having a mean wavelength of 4260 nm. A more accurate analysis indicates that the range consists of more than 80 narrow absorption lines produced by rotational transitions. These lines have a half-value width and a relative height which depend on a plurality of factors, such as temperature, pressure, and even collisions by other molecules included in a gas mixture. Temperature and pressure can be generally accounted for simply by measuring the same and by correcting the measuring signal with this result. On the other hand, a change resulting from collisions of other gas components, having an indirect impact on the concentration analysis, must be accounted for in a special way. The publication APPLIED OPTICS, Vol. 25, No. 14, pp. 2434–2439, 1986: C. Cousin et al.—"Air broadened linewidths, intensities, and spectral line shapes for $CO_2$ at 4.3 $\mu$m in the region of the AMTS instrument" describes changes on the half-value width of carbon dioxide in a nitrogen and oxygen mixture. The carbon dioxide line (ordinal 67) of a normal-pressure gas mixture has a half-width value which in an oxygen mixture is 0.055 cm$^{-1}$ (0.10 nm) and in a nitrogen mixture it is 0.060 cm$^{-1}$ (0.11 nm) for a concentration of 5% $CO_2$. The portion of a broadening caused by carbon dioxide to itself is only about 0.003 cm$^{-1}$ in these figures.

The polar gases like laughing gas or nitrous oxide ($N_2O$) have still a lot more influence on the half-value width. Therefore, the measurement of a carbon dioxide amount in the respiratory gases of a patient is subjected to a laughing gas correction for example by measuring the $N_2O$ concentration, as described in US-publication 4,423,739. The influence of oxygen as opposed to nitrogen is also often corrected, although the error is less serious. This type of correction method is not very good or even reliable but, in fact, the method requires that the concentrations of all gas components in a gas chamber and the influences of the gas components on collision broadening be known beforehand in order to perform the correction. The influences are not even unambiguous since the influence of a given gas in a gas mixture on the measurement may be different than the influence of the same gas alone. The measuring calculations necessitate highly extensive experimental information. The procedure described in the above-cited publication may provide a completely incorrect result, if a gas mixture to be analyzed is exposed to a previously unknown factor. As a result of such procedure, the measurement of all gases e.g. in a clinical patient monitoring situation will be generally highly expensive, if there is no other special reason for measuring these gas components.

The procedures described in the publication U.S. Pat. No. 3,745,349 and in other cited publications are not capable of solving the above problem without thoroughly understanding the phenomenon, nor have said publications even addressed the problem or sought a solution thereto. Hence, the above methods, intended for the sensitization of measurements to a given gas component, make use of a powerfully absorbing gas-filled band rejection filter, whereby the collision broadening and its influence cannot be measured. In addition, since the gas filter chamber is sealed and stationary as well as the fact that it contains a different gas composition and possibly a different pressure and temperature than those existing in the measuring chamber, the influence of collision broadening of absorption lines without a special dimensioning of the measuring chamber and filter chamber is difficult to account for. The accurate measuring results shall thus include errors, since the measuring systems as such do not tolerate a simultaneous measurement or correction of collision broadening during the course of measuring the concentration of a gas mixture.

The publication U.S. Pat. No. 4, 110,619 seeks to address the problem by attempting to completely eliminate the effect of collision broadening. The publication discloses both a so-called "dual-beam" arrangement, wherein a measuring chamber and a reference chamber and subsequent detectors are in parallel, and a so-called "single-beam" arrangement, wherein the detector is common for both signals and the signal of a measuring and reference chamber is separated by passing the radiation through the chambers after pulsing it e.g. with a chopper. The detector itself includes two separate, yet coupled-together, gas-filled chambers, wherein the absorbed radiation causes pressure changes that are measured e.g. with a sensitive microphone. The elimination of collision broadening is based on setting the gas sample of the detector chambers, the amount of gas, or the length of the chambers to be such that the composition of a gas mixture, i.e. the collision broadening effects, would not alter the actual measuring signal. As noted quite correctly by the author of the publication, the principle only applies to a sufficient degree in a so-called "single-beam" arrangement, but even in this the gas sample must be set such that, concurrently, the measuring sensitivity for a particular gas to be measured decreases, the stability of a null point suffers, and the sensitivity for measurement-disturbing other gases increases. In addition, since the so-called "single-beam" arrangement in fact includes three successive radiation-absorbing chambers (a measuring chamber and two detector chambers), which must be simultaneously brought to the required balance in terms of absorption, the compensation for influence of collision broadening is only possible for one given concentration of a gas to be measured. In the example disclosed in the publication, which describes a calibration procedure included in the method, this concentration is 10% $CO_2$. Over other concentrations, the compensation for collision broadening is no longer satisfactory and, thus, the problem caused by collision broadening remains. The above phenomenon is due to the fact that the gas mixture in the measuring chamber also affects the radiation falling on the detector by changing its spectral shape at the absorption line. Since the adaptation of the amount of gas in the detector chambers is based on this very balance between the peaks and side slopes of an absorption line, which is thus also affected by a gas in the measuring chamber, there will be an error if deviation is made from a so-called calibration concentration. Hence, in a general sense, this type of compensation procedure cannot be a satisfactory solution for eliminating the error of a collision broadening. The use of pneumatic, bulky, and somewhat insensitive, and in this case also very specially designed detectors is as such unfit for modern times.

As simplified, the total absorption of gas is proportional to the number of gas molecules in a measuring volume. This is the case, especially if the sample chamber, and particularly its length, is small in the direction of infrared radiation. Thus, the inherent absorption of gas does not essentially alter the effect of radiation applied to each molecule. The radiation applied to a molecule may change as a result of the self-absorption of a gas to be measured in a gas mixture or other absorbing components within the same radiation band. The direct influence of such other components on the gas to be analyzed is generally eliminated in such a manner that the spectral band of radiation to be studied is limited within a wavelength range over which the gas to be analyzed is the only one to absorb. The remaining problem is that other gas components, as pointed out above, have an effect on the absorption of a gas to be measured also as a "distant effect", i.e. by way of collision broadening, whereby the restriction of a measuring band does not help. In collisions, the energy distribution of a molecule is slightly changed, resulting in the broadening of an absorption line. However, the absorbancy value of a molecule integrated across the line remains practically unchanged. The non-dispersive infrared technique is unfortunately incapable of directly measuring absorbancy, but the transmission of infrared radiation is measured over an entire selected wavelength band. Indeed, the transmission of infrared radiation as such is generally a better quantity for representing absorption in practical measuring systems, which employ a wavelength band of a reasonable width, than the absorbancy itself, which is more applicable to cases in which the measuring is done over a very narrow wavelength band and in which the sample chamber is also preferably small.

When measuring non-dispersively over a given wavelength bandwidth, a total transmission Tm will be an integral across a filter spectral range $\lambda 1 - \lambda 2$:

$$Tm = \int_{\lambda 1}^{\lambda 2} F(\lambda) \cdot T(\lambda) d\lambda$$

wherein $F(\lambda)$ is a transmission function for the filter and $T(\lambda)$ is a transmission depending on the wavelength of a gas sample. Usually the transmission Tm no longer follows the Lambert-Beer law, although this is the case over one wavelength $T(\lambda)$.

In such a situation that the radiation advances in a long gas-filled conduit, $F(\lambda)$ represents that wavelength distribution of incoming radiation which falls on a section of the conduit subject to examination. As a result of this, both $F(\lambda)$ and $T(\lambda)$ are also functions of place. Hence, the transmission must be monitored also locally in order to understand the signal Tm measured over the entire measuring conduit.

The first aspect of examination is how the wavelength distribution of radiation influences the magnitude of an error caused by collision broadening. As a matter of fact, the magnitude of the error of Tm depends on the bandwidth of a filter, i.e. the very characteristics of $F(\lambda)$. If measuring is done over a wavelength band of a suitable width, which is in the same order as the width of a single absorption line, the correction requirement of collision broadening is very insignificant or non-existent. This is disclosed for example in EP-publication 0,405,841, wherein carbon dioxide is measured by using a narrow-band source of carbon dioxide radiation. This is equivalent to an optical filter, which includes a plurality of transmission bands corresponding to absorption lines of carbon dioxide. On the other hand, if the optical filter has a transmission band which is narrower than the width of an absorption line to be measured, the collision broadening will cause a reduction of absorption as the peak of the absorption line becomes lower. Such a case is described in WO-publication 94/24528, wherein a single absorption line of oxygen is measured with a highly narrow-band laser diode. Thus, the Lambert-Beer law applies in terms of the laser wavelength and, by scanning the wavelength (which can be done e.g. by changing temperature of the laser diode) over the entire absorption line, it will be possible to calculate the absorbancy across the entire wavelength range and, thus, the collision broadening no longer has an essential effect on the final result.

If the filter has a transmission band which extends over a number of absorption peaks, which is usually the case when measuring carbon dioxide, there is a need for correction since the total absorption increases as the collision broadening increases. This is a common condition in practical measurements.

As already pointed out, the concentration analysis is also affected by the length of a measuring conduit. With a short conduit, the demand of correction is lesser, while with a longer conduit, wherein the absorption of a gas to be measured has reduced transmission substantially more, the demand of correction may be considerable. In the carbon dioxide measurement for the respiratory or alveolar gases of a patient, wherein for example during the course of anesthesia a substantial portion of the gas mixture may consist of nitrous oxide (laughing gas, $N_2O$), the calculated $CO_2$-gas concentration may be up to 15% too high as a result of the above-described error caused by a transmission integral. Furthermore, if the measuring system involves a measurement of several different gas components in one and the same measuring chamber, the dimensioning of a chamber length is always a compromise, the principal sufferer being the absorbing gas component for which the chamber is hence too long. In this type of situation, the need of correcting the collision broadening is extremely grave, especially if the sum of gas components has been forced mathematically to a certain level, e.g. to 100%, whereby the incorrect concentration analysis of a single gas component affects also the analyses of other gases.

BRIEF SUMMARY OF THE INVENTION

A primary object of this invention is to provide a method and a sensor device for accurately determining the influences of the above-described collision broadening of absorption lines. A second object of the invention is the accurate measurement of the concentration of a desired gas component in a non-dispersive, radiation-absorption based measuring system, wherein no other measuring information is available regarding the composition or other nature of a gas mixture to be analyzed. A third object is to provide a method and a sensor device, which functions over a wide concentration range of a gas component to be measured regardless of the nature of a mixture gas. A fourth object is a method and a sensor device, which functions both in so-called "single-beam" and "dual-beam" arrangements. A fifth object is to provide also a procedure for dimensioning a gas-filled optical filter and a measuring chamber used in infrared-absorption measurements, such that the correction of collision broadening can be calculated unambiguously. A sixth object is to provide also a procedure for dimensioning a gas-filled optical filter and a measuring chamber used in infrared-absorption measurements, such that the concentration of a desired gas component can be calculated accurately. A seventh object is to provide a method and a sensor device, wherein the errors resulting from the effects of pressure and/or temperature are as insignificant as possible and readily correctable. An eighth object is a method and a sensor device, which is applicable in a gas mixture for measuring a variety of gas components and simultaneously for the measurement of collision broadening effected by especially by one or possibly by more than one gas components, the result thereof being used for correcting the analysis of a gas concentration. A ninth object is a method and a sensor device, which can be used for accurately measuring a plurality of gas components simultaneously by means of a single measuring chamber regardless of the various absorption levels of gas components and of the fact that for the most intensely absorbing component the compensation of collision broadening would be quite substantial. A further object is a method and a sensor device, which is simple, reliable, and inexpensive. A yet another object is a method and a sensor device, which is adaptable to the analysis of the respiratory gases of a patient in a patient monitoring situation.

BRIEF DESCRIPTION OF THE SEVERAL VIEWS OF THE DRAWING

The invention will now be described in detail with reference made to the accompanying figures.

FIG. 2A illustrates diagrammatically an absorption band included within the infrared range of one exemplary molecule and its fine structure constituted by a plurality of absorption lines of unequal sizes and unequally spaced from each other.

FIGS. 2B and 2C illustrate diagrammatically a transmission of radiation corresponding to the absorption band of FIG. 2A, visualizing a plurality of narrow radiation stop bands which correspond to the absorption lines of FIG. 2A. FIG. 2B depicts a typical gas-filled optical band rejection filter of the invention, which eliminates on average about 20% of the incoming radiation, i.e. transmission of the filter averages about 80%, and by means of which it is possible to investigate collision broadening. FIG. 2C, on the other hand, depicts transmission of a typical sensitizing gas-filled band rejection filter, dimensioned to a given gas component and of the above-described type, which in this case averages only about 45%.

FIGS. 3A–5B illustrate the effects of collision broadening calculated according to one simple model. FIGS. 3A–5A shows the change of transmission as a function of the absorption line width when the signal of FIG. 1B is measured through an optical bandpass filter having only a narrow transmission band. Accordingly, in FIGS. 3B–5B the signal of FIG. 1B is measured through a narrow-band optical band rejection filter. In all these figures, transmission is normalized as numeral one for a non-broadened absorption line. In FIGS. 3A–3B the total transmission of radiation in a hypothetical measuring chamber is 78%, in FIGS. 4A–4B 68%, and in FIGS. 5A–5B 55%. The horizontal axes depict a relative half-value width for the absorption line, which is normalized as numeral one for a non-broadened absorption line.

FIG. 11D shows the sixth embodiment for the device which, in addition to the above-mentioned components, includes a second gas-filled band ejection filter, whereby is obtained the third signal S3. These are used for determining both the $CO_2$-concentration and a parameter indicative of collision broadening.

DETAILED DESCRIPTION OF THE INVENTION

Figure 1A:
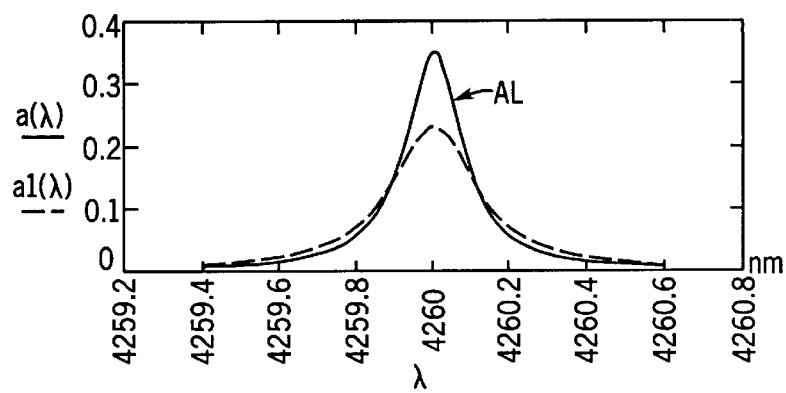
FIG. 1A illustrates the relative absorption efficiency of a single absorption line within one absorption spectral band of carbon dioxide on a logarithmic scale, i.e. the absorbancy, as a function of wavelength. The absorption line has a non-broadened shape (AL) shown with a solid line and a shape broadened as a result of the collision broadening caused by a mixture gas shown with a dash line. The absorption lines have an equal surface area and follow a so-called Lorentzian profile.
Figure 1B:
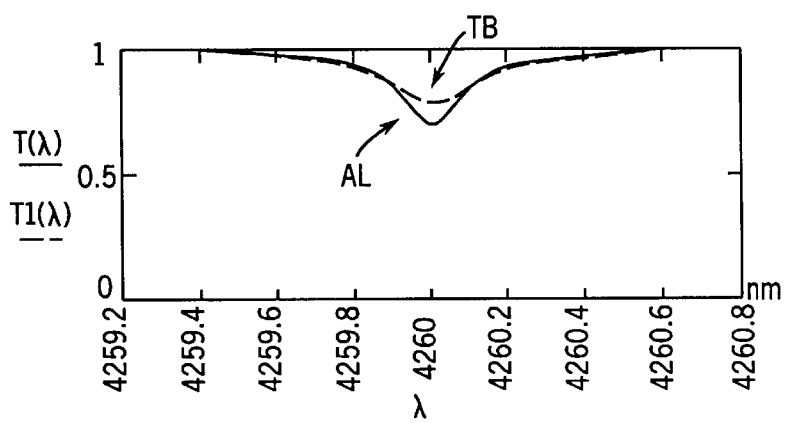
FIG. 1B illustrates the behavior of the absorption line of carbon dioxide as shown in FIG. 1A in a transmission form, the vertical axis depicting transmission and the horizontal axis depicting wavelength. The absorption line has a non-broadened shape shown with a solid line and a shape broadened as a result of the collision broadening caused by a mixture gas shown with a dash line (TB).

In order to be able to roughly describe a real gas measuring system at various widths of an optical bandpass filter, the examination is only concentrated on one of the peaks of the rotational line of one absorption band. In FIG. 1A, such an absorption line AL is depicted as a function of wavelength $\lambda$ (nm) and, likewise, as a length-correlated absorbancy $a(\lambda)$ as well as $a1(\lambda)$ for two different half-value widths of the absorption line (with a solid line 0.1 nm and with a dash line 0.15 nm). In FIG. 1B, the same absorption line is shown as a transmission $T(\lambda)$ and $T1(\lambda)$ visible to the measuring system and intended for the corresponding two different half-value widths of the line (with a solid line 0.1 nm and with a dash line 0.15 nm). As depicted in FIG. 1A, the absorption peak becomes lower as the width increases, yet in such a manner that the total area remains unchanged. Although this is not readily visible in FIG. 1B, the area of an absorption band TB visible to the measuring system increases as the line broadens. In FIG. 1A, the absorption line is modeled according to a Lorentzian profile. The condition shown in FIGS. 1A and 1B illustrates absorbancy and radiation transmission in the event that absorption is very slight or only about 5% of the incoming radiation has disappeared, mainly at the absorption peak.

FIGS. 2A–2C illustrate diagrammatically a real situation for one gas molecule. FIG. 2A shows how the absorption lines of a gas molecule have developed into an absorption band, wherein the absorption lines are unequal and at a random distance from each other. Thus, the absorption band of a molecule is a comb-shaped or pectinated constitution, the elements of which are constituted by single absorption lines. The shape and relative magnitude of absorption lines are particularly influenced by temperature and also by collisions of gas molecules with each other. FIG. 2B shows how radiation penetrates a thin gas layer in the event that the gas layer contains such molecules. The gas layer functions as an optical band rejection filter, which eliminates radiation first mainly at the very peaks of absorption and thereafter, as radiation advances within the gas layer, also off the flanks of the absorption line. In FIG. 2B, the radiation has an ultimate total transmission of about 80% which, moreover, is concentrated between absorption lines. This is a preferred configuration for a gas-filled filter as far as the present invention is concerned. FIG. 2C shows a gas-filled optical filter in a configuration which is preferable whenever it is desirable to provide a certain reference for the gas measurement or if the measurement is sensitized for this particular gas molecule. In FIG. 2C, the infrared radiation has a transmission of about 45%, at which level nearly all radiation has been eliminated at the absorption line of the molecule. At this point, the same molecule contained in a measuring chamber no longer attenuates the radiation transmitted through the filter. Since such radiation is no longer sensitive to the concentration of the actual molecule, neither is it sensitive to the width of its absorption line. Thus, in terms of measuring collision broadening, it is necessary, in accordance with the invention, to employ mildly absorbing gas-filled optical filters.

Supposing that a single line of reduced transmission in FIG. 1B is measured with a bandpass filter, having a transmission band which is ideal, in other words the band has edges which are sharp, and over a passband, i.e. at the absorption line to be measured, transmission is 100% and over a stop band, i.e. outside the passband, transmission is 0%. This represents a condition, wherein the transmission of a gas contained in a measuring chamber takes the profile 1B and wherein the transmission is measured with a detector, in front of which is set an ideal bandpass filter of the above type. The condition is illustrated in FIGS. 3A–5A. Alternatively, the same transmission of FIG. 1B can be measured through an ideal band rejection filter, wherein, thus, over a stop band, i.e. at the absorption line to be measured, transmission is 0% and over a passband, i.e. outside the stop band, transmission is 100%. The condition is illustrated in FIGS. 3B–5B. Hence, FIGS. 3A–5B illustrate the expectable measuring signals for various filter widths=0,1, 1,2 and 4 as well as for various absorption linewidths=1, 1.1, 1.2 and 1.3 whenever the radiation in a measuring chamber has a total transmission of 78%, 68% or 55%. The measuring signals are presented in the form of relative transmission Tm/Tm(1) or normalized with a transmission which is measured at a non-broadened absorption line. The horizontal axis depicts a relative parameter indicative of the width of an absorption line. The half-width of the non-broadened line has an arbitrary value 1. The pass- or stop bandwidth of a very narrow filter has been given a relative value 0.1 (solid line) and the width of wider filters has been given values 1 (solid line), 2 and 4 (dash lines). In reference to carbon dioxide, the average distance of adjacent absorption lines from each other in these same units is 10. In practice, a filter corresponding to the bandwidth 0.1 (equals in reality to a wavelength band of about 0.01 nm) is not possible to construct, but a similar effect could be accomplished with laser techniques. In this context, the curve is intended to illustrate the basic behavior of radiation, should such a filter exist.

As shown in FIGS. 3A–5B, the signal generally diminishes as the absorption linewidth increases. The exception is a very narrow bandpass filter, wherein, at least in the case of the applied absorption model, the transmission of radiation increases as the linewidth increases. In all band rejection filters the signal diminishes. Likewise, it should be noted that if the length of a measuring chamber or the concentration of a gas contained therein increases, the collision broadening has an increased effect on the transmission of radiation. Thus, for a long chamber, the collision broadening corrections are always more extensive than for a short chamber. This and also the magnitude of correction are well compatible with experimental discoveries.

One way of compensating for an error caused by the broadening of an absorption line in the determination of a carbon dioxide concentration or some other gas component in a gas mixture to be analyzed could be the effort of producing a signal independent of collision broadening. This is indeed possible at one given gas concentration of a measuring chamber, i.e. at one transmission level, as well as by suitably combining therewith various filters or by specially dimensioning the absorption chambers of a detector. However, the result would only be a partial solution. This can be well ascertained from FIGS. 3A–5B, which illustrate the fact that the influence of collision broadening, i.e. the required compensation, is clearly dependent on the concentration of a gas or the transmission of radiation.

The basic principle of this invention is that changes caused by collision broadening in the transmission of radiation are in fact maintained in the form of a signal the same way as changes caused by the concentration of a gas to be measured. These changes are determined with empirical methods in the form of a mathematical relationship, which includes at least two signals S1 and S2 as well as two unknown variables, i.e. a gas concentration C and a parameter T indicative of collision broadening. The thus developed cluster of equations is finally solved unambiguously for both an accurate gas concentration and collision broadening. Hence, this novel method does not seek to come up with any compensation or such a measuring system in which the collision broadening would not influence the signal. As a matter of fact, the most preferred case is that the collision broadening would influence one of the signals as much as possible.

FIGS. 3A–5B illustrate further that, in the case of a band rejection filter, the effect of collision broadening on a signal is at its highest when the band rejection filter has a width of 1–2 units, i.e. the stop band is in the same order as the width of the actual absorption line. Such a gas-filled filter removes typically about 20% of the amount of radiation falling on the filter, as we shall subsequently find out.

Those prior art solutions, which were intended to sensitize the measurement to a specified gas component, require that the degree of fullness of a gas-filled filter be preferably such an amount that nearly all radiation or, according to some publications, as much of the radiation as possible will be absorbed in the filter. Therefore, this gas-filled filter optimized according to the invention for the measurement of collision broadening cannot be regarded as a reference or a measurement sensitizing component in the same sense as in the available prior art. According to publications describing the prior art, the stop band must be typically capable of eliminating more than 50% of the radiation arriving at the band rejection filter. This means that the filter must have an effective stop band which is about half of the average distance between adjacent absorption lines, i.e. more than 5 in units set forth in this specification. In terms of the measurement of collision broadening, it is most preferable according to the invention that the stop band of a filter be dimensioned to have a width of 1–2 units. Hence, this means that the stop band of a filter, such as an optical gas filter, must have a width which is 1–2 times the half-value width of a non-broadened absorption line.

In order to explain even in more detail the fundamentals of the novel invention, the novel method is studied from another perspective, i.e. the propagation of radiation is monitored in a long measuring-gas filled tube or duct. As the radiation advances, its wavelength distribution changes constantly and gas molecules located in a different section of the tube are exposed to a differently distributed radiation exciting and leading the same to absorption. At the very inlet end of the tube occurs the elimination of such radiation wavelengths, at which there are peaks of the absorption lines of a medium gas. At the downstream end of the tube remains only such radiation, which settles along the low sections of absorption lines in terms of its wavelength. Thus, the inlet end and outlet end of the tube are in a totally different position and for example the collision broadening manifests itself in different ways depending on which part of the tube is in question. This behavior leading to novel device configurations of the invention is further illustrated in FIGS. 6A, 6B and 7.

Figure 6A:
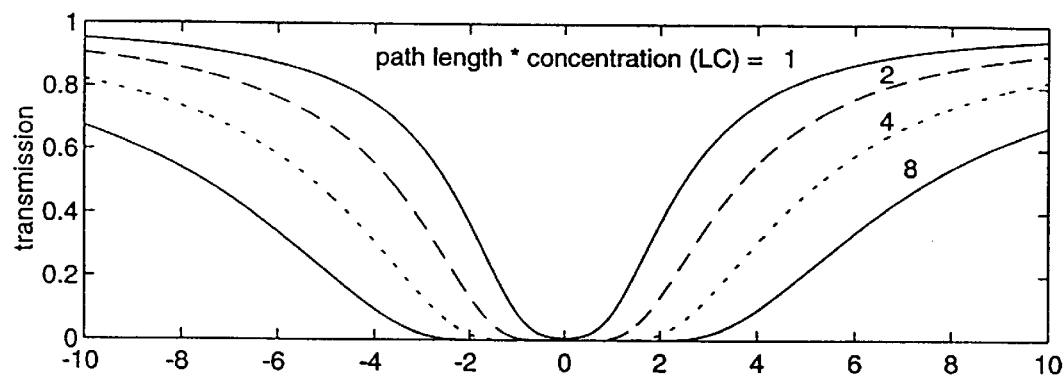
FIG. 6A shows at a single absorption line the distribution of the intensity of radiation passed through a gas-filled band rejection filter or a long measuring chamber as the radiation advances in the band rejection filter or measuring chamber, the vertical axis depicting a relative transmission, the horizontal axis depicting a relative wavelength within the range of −10 . . . +10 normalized to the half-value width of a non-broadened absorption line, such selected value being=1. The symbol alongside the curves carries a number indicative of a radiation path length LC=1, 2, 4 and 8, which is a product of the real path distance and the gas concentration whereby, with the distance LC=1, over the entire discussed wavelength range the radiation has been absorbed by 1/3 at a non-broadened absorption line.

FIG. 6A shows an intensity passed through an optical gas-filled band rejection filter or a long measuring chamber in terms of its distribution at a single absorption line with radiation propagating in a band rejection filter or a measuring chamber, the vertical axis depicting a relative transmission and the horizontal axis depicting a relative wavelength as normalized to the width (=1) of a non-broadened absorption line. Alongside the curves is indicated a radiation path length LC=1, 2, 4 and 8 normalized in such a manner that at the path length 1, over the entire monitored wavelength range, 1/3 of the radiation has been absorbed at a non-broadened absorption line. According to FIG. 6A, the full linewidths measured at the transmission level 0.5 of a radiation stop band are, in terms of relative wavelength units, at the path length LC=1 about 5.2, at the path length LC=2 about 7.5, and at the path length LC=8 about 15 units. All said stop band widths are clearly in excess of the full width of the absorption line of a single gas molecule, i.e. 2 units (the unit being a half-value width in a Lorentz curve 1). Moreover, it should be noted that, if the inlet end of a long duct were used, in the sense of the novel invention, as a preferred gas-filled filter, the length of the inlet end of a filter should be determined to be less than LC=1.

Figure 6B:
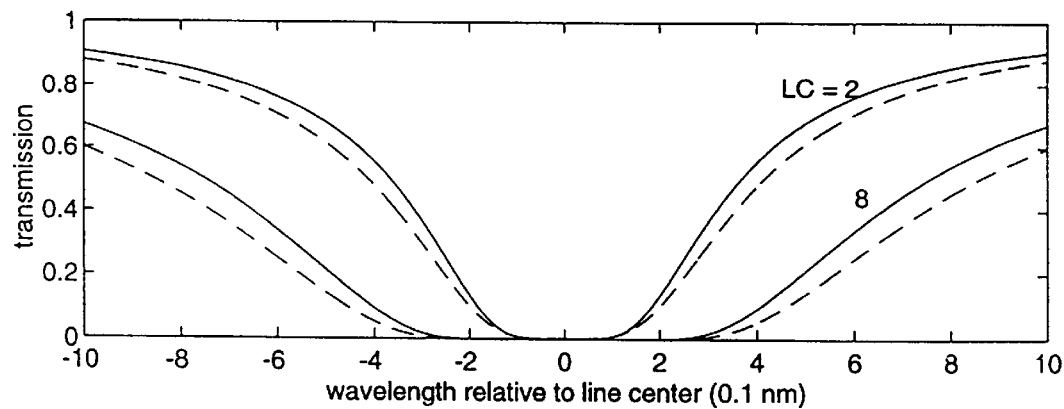
FIG. 6B illustrates the transmission curves of FIG. 6A at two different distances, i.e. LC=2 and LC=8, in the event that the absorption line has not broadened (shown with a solid line, wherefor the relative absorption linewidth=1) and in the event that the line has broadened (shown with a dash line, wherefor the relative absorption linewidth=1.3).

FIG. 6B illustrates the effect of line broadening on the transmission curves of FIG. 6A. FIG. 6B includes two transmission curves at two different path lengths (LC=2 and LC=8). The pair of curves has an upper solid line for the event that the absorption line is not broadened (i.e. the relative half-value width=1) and a lower dash line for the condition that the line has experienced a relatively intensive broadening (the relative half-value width=1.3). FIG. 6B manifests the previously established fact that the collision broadening influences the determination accuracy of a gas concentration measurement more intensely in a long measuring chamber.

Figure 7:
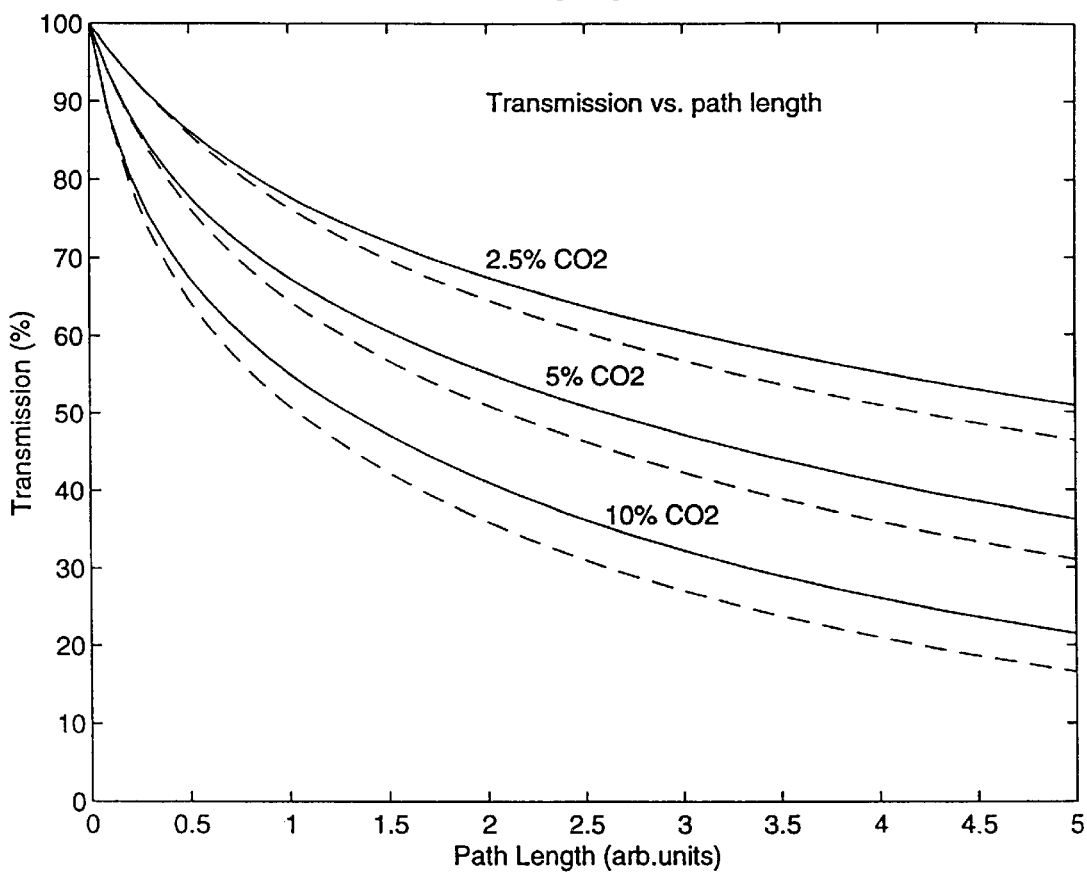
FIG. 7 illustrates the integrated intensity of transmitted radiation within the discussed wavelength range as a function of distance for three different gas concentrations and two absorption linewidths, for a non-broadened absorption line (shown with a solid line, relative width=1), and for a distinctly broadened absorption line (shown with a dash line, relative width=1.3).

FIG. 7 illustrates a total transmission measured across the monitored wavelength range as a function of the path length LC measured from the end of a tube. The figure shows three pairs of curves, which differ in terms of a gas concentration and for which the relative magnitudes of collision broadening T are 1 (solid line) and 1.3 (dash line). At all path lengths, the collision broadening increases the gas absorption. The increase of absorption is almost non-existent at the very inlet end of the tube, the radiation eliminated by absorption corresponding to about 20% of the incoming radiation. By then, however, the spectrum of transmitted radiation has dramatically changed.

One concept of the novel invention is that by fitting a relatively long sample chamber with at least two detectors, mounted to measure transmission at two different path lengths from the inlet end of the sample chamber, it is possible to produce two linearly independent signals, which nevertheless have a mutual relationship and which can be used for unambiguously calculating both a gas component concentration and collision broadening. This is indeed possible since in various parts of the sample chamber the gas component molecules experience a different radiation wavelength distribution. Subsequently, this text will deal with carbon dioxide as one example of such a gas molecule. It should be appreciated that what is discussed above applies also to any other optically active gas molecule.

Figure 8A:
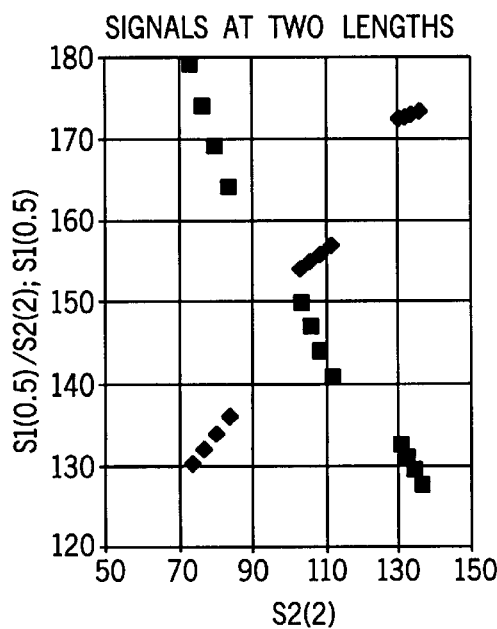
FIG. 8A depicts one way of producing two signals S1 and S2, which are measured at two different measuring chamber lengths—in this case at normalized lengths S2=2 and S1=0.5. The horizontal axis depicts the signal S2 and the vertical axis a ratio S1/S2 of said two signals in percentage or just the signal S1 normalized as in the preceding figures. As for the first cluster of dots on the left-hand side of the figure, wherein the signal S2 is between 70–90, the carbon dioxide concentration is high, corresponding in terms of its absorption to about 10% concentration in a chamber having a length of about 5 mm. As for the next central cluster of dots, wherein S2 is between 100–120, the carbon dioxide concentration is half, i.e. 5%, of the concentration of the first cluster, and as for the third, right-hand cluster of dots, wherein S2 is between 130–140, the carbon dioxide concentration is a fourth, i.e. 2.5%, of the concentration of the first cluster of dots. Each concentration is represented by the signals S1 and S1/S2 in the form of dots in said set of coordinates for four different relative linewidth parameters 1, 1.1, 1.2 and 1.3. Lozenges for the signal S1 are such that a non-broadened line (absorption linewidth=1) is always represented by the highest dot of the cluster (highest transmission) and the subsequent dots in the order of size represent a change of the signal as the absorption linewidth increases, the lowest dot representing a strongly broadened absorption line. Squares are for the signal S1/S2, wherein, conversely, the highest point corresponds to the most intensely broadened absorption line, i.e. the dots having the same S2-value always constitute the pair of dots S1 and S1/S2 for one given condition.
Figure 8B:
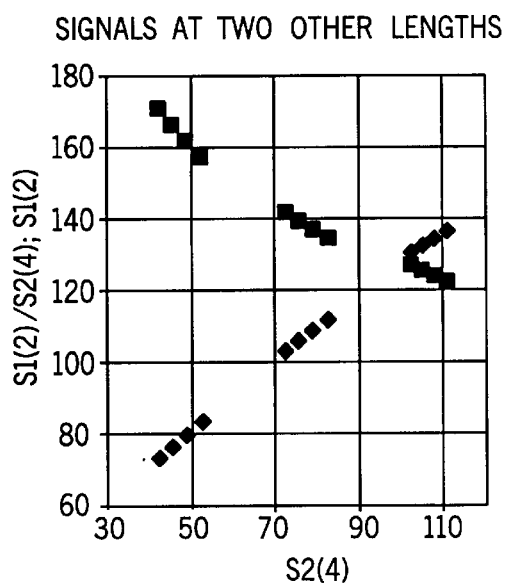
FIG. 8B shows another way of producing two signals S1 and S2, which are measured at two different measuring chamber lengths—in this case at normalized lengths S2=4 and S1=2. The horizontal axis depicts the signal S2 and the vertical axis a ratio S1/S2 of said two signals (in percentage) or just the signal S1 normalized as in the preceding figures. As for the first cluster of dots on the left-hand side of the figure, wherein the signal S2 is between 40–60, the carbon dioxide concentration is high, corresponding in terms of its absorption to about 10% concentration in a chamber having a length of about 5 mm. As for the next central cluster of dots, wherein S2 is between 70–90, the carbon dioxide concentration is half, i.e. 5%, of the concentration of the preceding cluster, and as for the third cluster of dots on the right, wherein S2 is between 100–120, it is a fourth, i.e. 2.5%, of the concentration of the first cluster of dots. Each concentration is represented by the signals S1 and S1/S2 in the form of dots in said set of coordinates for four different relative linewidth parameters 1, 1.1, 1.2 and 1.3. Lozenges for the signal S1 are again such that a non-broadened line (absorption linewidth=1) is always represented by the highest dot of the cluster (highest transmission) and the subsequent dots in the order of size represent a change of the signal as the absorption linewidth increases, the lowest dot representing a strongly broadened absorption line. Squares are for the signal S1/S2, wherein, conversely, the highest point corresponds to the most intensely broadened absorption line, i.e. the dots having the same S2-value always constitute the pair of dots S1 and S1/S2 for one given condition.
Figure 3A:
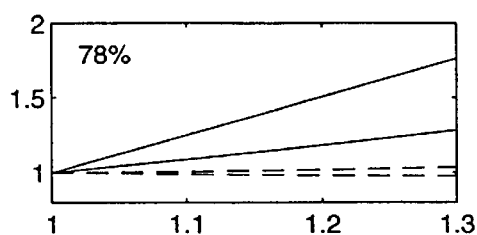
Figure 3B:
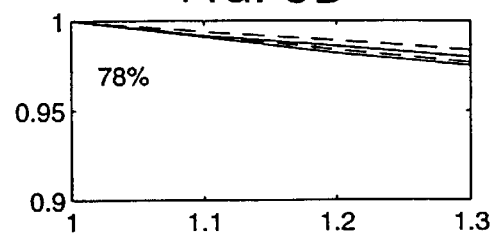
Figure 4A:
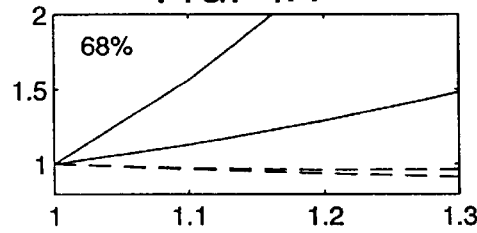
Figure 4B:
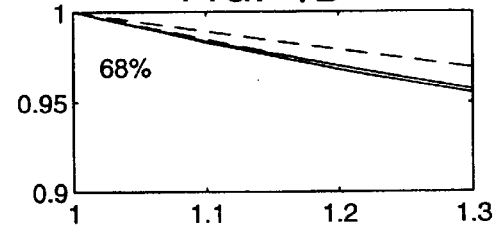
Figure 5A:
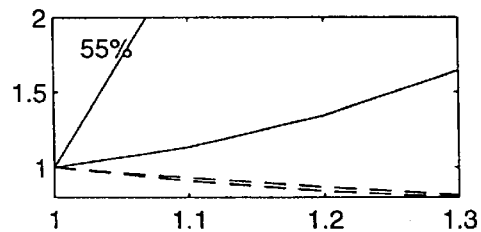
Figure 5B:
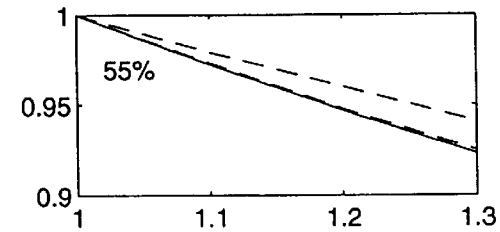

FIGS. 8A and 8B illustrate in different instances the behavior of thus developed signals. Hence, FIG. 8A shows one way of producing two signals S1 and S2, measured at two different measuring chamber path lengths—in this case at normalized path lengths S2=2 and S1=0.5. The horizontal axis carries the signal S2 and the vertical axis a ratio S1/S2 (in percentage) of said two signals or the signal S1 alone and normalized as in the preceding figures. As for a first cluster of dots on the left in the figure, wherein the signal S2 is between 70–90, the carbon dioxide concentration is high (corresponds in terms of its absorption to the concentration of about 10% in a chamber with a length about 5 mm). As for the next central cluster of dots, wherein S2 is between 100–120, the carbon dioxide concentration is half (5%) of that of the first cluster, and for a third cluster of dots on the right, wherein S2 is between 130–140, it is a fourth (2.5%) of the concentration of the first cluster of dots. Each concentration is represented by the signals S1 and S1/S2 in the form of dots in said set of coordinates for four different relative linewidth parameters 1, 1.1, 1.2 and 1.3. Lozenges are for the signal S1 such that the non-broadened line (the half-value width of an absorption line=1) always corresponds to the highest dot in a cluster (highest transmission) and the subsequent dots in the order of size to a signal change as the width of an absorption line increases, the lowest dot corresponding to a dramatically broadened absorption line. Squares are for the signal S1/S2, wherein the highest dot to the most dramatically broadened absorption line, i.e. the dots with an equal S2-value always constitute a pair of dots S1 and S1/S2 for a single particular condition.

FIG. 8A shows that each individual signal S1 and S2 changes vigorously as the carbon dioxide level changes. In addition, the ratio S1/S2 of the signals changes dramatically as the collision broadening changes, even though the carbon dioxide level remains constant. Combining these two signals together produces unambiguously both carbon dioxide concentration and collision broadening. The linear independence of the signals can be ascertained without major calculations for example in such a manner that, at the carbon dioxide level of 10%, the signal S1 (can be regarded as a primary $CO_2$-signal) changes by 5% as opposed to the "collision broadening signal" S1/S2 which changes by 10%. The linear independence is also clear on the basis of theory since, after all, these signals do behave at least to some extent as requested by the Lambert-Beer law. If the situation is studied in the similar fashion from FIG. 8B, it will be noted that also the geometry of a measuring chamber influences the nature of the signals and that there exists a given optimal arrangement for a given required measuring range of $CO_2$, e.g. 0%–10% $CO_2$. Within this cited $CO_2$-range, the arrangement of FIG. 8A is slightly better than that of FIG. 8B, since in FIG. 8A both signals S1 and S2 and, on the other hand, the relative changes caused by collision broadening in the ratio of the signals surpass those of FIG. 8B. The arrangement of detectors is implemented according to the invention, as subsequently described.

The novel measuring method can be presented mathematically as a solution to the following non-linear cluster of equations $$\begin{pmatrix} S1 \\ S2 \end{pmatrix} = \begin{pmatrix} A_{11}(S1,S2) & A_{12}(S1,S2) \\ A_{21}(S1,S2) & A_{22}(S1,S2) \end{pmatrix} \begin{pmatrix} C \\ dT \end{pmatrix} \quad (I)$$

wherein S1 and S2 are said two signals at different path lengths from the inlet end of a measuring chamber and C is a carbon dioxide concentration and dT a parameter indicative of collision broadening. The cluster of equations is non-linear, which is manifested by the fact that the matrix coefficients are functions of the signals themselves or, alternatively, functions of $CO_2$ and dT. It should also be noted that coefficients $A_{ij}$ are dependent on measuring geometry. The cluster of equations can be solved iteratively or by experimentally finding appropriate coefficients $A_{ij}(S1, S2)$, whereafter the cluster of equations is solved by standard textbook methods.

Subsequently, we study the novel measuring method apportioned in typical method sequences. As for these sequences, those to be carried out prior to analyses are: 1) selection of a measuring geometry and a preferred arrangement of detectors in a measuring chamber, 2) a measurement calibration sequence by using a variety of gas mixtures and a variety of carbon dioxide concentrations, 3) a calibration data storage sequence, wherein the coefficients associated with the measuring geometry and the selected mathematical method of solving a non-linear cluster of equations are stored for subsequent use. Then follow 4) an actual measuring, i.e. sequences which are carried out during the analyses and which no longer require any information about a gas mixture to be used and which involve the production of two or more measuring signals useful for determining both the carbon dioxide concentration and a parameter indicative of collision broadening, and 5) a calculation sequence, wherein the exact carbon dioxide concentration is determined accompanied with the correction of collision broadening. As for the above five method sequences, the calibration sequence and calculation sequence are interrelated with a mathematical method selected for solving the cluster of equations. Hence, the method of the invention includes sequences carried out beforehand prior to the actual analyses for providing the measuring system with correct set-up data and sequences carried out during the course of analyses for extracting measuring results M from the actual gas mixture to be examined.

The selection of a measuring geometry is particularly influenced by the range of carbon dioxide concentration the measurement is optimized for and by the magnitudes of linewidth corrections expectable with gas mixtures involved in the practical measurement. Generally, for a low carbon dioxide concentration (0–10%) is selected a long chamber (5–20 mm) and for a high concentration (10–100%) a short chamber (0.5–5 mm). Usually, i.e. whenever it is desirable to have a powerful signal depending on the $CO_2$ concentration, the chamber length is preferably determined to be such that, at the top end of a precision-demanding measuring range, e.g. in medical measurements of a respiratory gas at the concentration of about 10% $CO_2$, the signal of a detector furthest away from a light source, i.e. S2, is no more than about 60%, preferably no more than about 40%, and typically 5–30% of what it is at the corresponding point on the lower threshold of the measuring range, i.e. at the concentration of 0% $CO_2$. The signals measured at the same $CO_2$ concentration, but at two different path lengths, have, as a result of the broadening of an absorption line, a ratio which increases as the distance between detectors increases. Thus, the detector closest to a light source is placed in such a fashion that a necessary resolution for the linewidth does exist. Preferably, the detector is located in such a manner that, in the middle of a $CO_2$ measuring range, thus e.g. at the concentration of 5% $CO_2$, the signal S1 is only diminished by about 5–50% and typically by 10–30% of what it is at the very start of a radiation path. With such an arrangement, the signal S1 has only relinquished those wavelengths which are exactly at the peak of an absorption line. This enables the highest possible resolution for the measurement of line broadening. In the above-described two-detector measuring system, the primary $CO_2$-signal S2 develops from the detector furthest away from a light source and the primary linewidth parameter is obtained e.g. from the ratio S1/S2 between signals of the detectors. By dimensioning a measuring duct as set forth above, it is possible to provide both measuring quantities, i.e. the amount of $CO_2$ and the linewidth, with a high resolution. The arrangement described in this paragraph is particularly useful in the devices shown in FIGS. 9A and 9B as well as 10A and 10B.

As an alternative for the arrangement described in the previous paragraph, it is possible, according to the invention, to arrange the detectors such that the second signal S2 has a magnitude which is 50–95% or 105–200% and preferably 70–90% or 110–140% of that of the first signal S1. This achieves the very same result as described above. This configuration is particularly useful in the devices shown in FIGS. 11A–12.

The second sequence of the measuring method involves the determination of measurement calibration data, which are subsequently used in the measurement of a $CO_2$ gas concentration effected in an unknown gas mixture. The calibration data is always determined in relation to a selected calculation method, i.e. the calibration measurements are carried out in such a measuring system and by such a mathematical procedure which are also used in the actual measurement. In any event, the calibration sequence involves measurements, wherein the $CO_2$ concentration and the gas mixture are varied for finding a mathematical relationship between the signals S1 and S2 as well as with the $CO_2$ concentration and the broadening of an absorption line without any special knowledge about a gas mixture. The next paragraph introduces one preferred way of finding out correlations of the signals S1 and S2 with respect to quantities to be determined. Subsequently, the calculating sequence shall be presented the same way as such a calibration sequence. The novel measuring method is not limited to the described calibration and calculation sequences, but these are presented as the most preferable example of what type of mathematical formalism is available.

Procedures required in the calibration sequence are best manifested, if the measuring signals S1 and S2 are first written as follows:

$$\begin{pmatrix} S1 \\ S2 \end{pmatrix} = \begin{pmatrix} B_{11}(C,T) & B_{12}(C,T) \\ B_{21}(C,T) & B_{22}(C,T) \end{pmatrix} \begin{pmatrix} C \\ T \end{pmatrix} \quad (II)$$

wherein matrix coefficients $B_{ij}$ are now shown as a function of the $CO_2$-concentration (designated with letter C) and the linewidth (T). Written for the signals S1 and S2 is a Taylor expansion at a known $CO_2$-concentration CO and in a given gas mixture (e.g. nitrogen), wherein the linewidth change reaches its nominal value T0=0 (note that T is thus the linewidth change dT with respect to this gas mixture and it can be both positive and negative in other gas mixtures):

$$\begin{pmatrix} S1 \\ S2 \end{pmatrix} = \begin{pmatrix} S1(C0, T0 = 0) \\ S2(C0, T0 = 0) \end{pmatrix} + \begin{pmatrix} \frac{\partial S_1(C0, T0)}{\partial C} & \frac{\partial S_1(C0, T0)}{\partial T} \\ \frac{\partial S_2(C0, T0)}{\partial C} & \frac{\partial S_2(C0, T0)}{\partial T} \end{pmatrix} \begin{pmatrix} dC \\ dT \end{pmatrix} + \quad \text{(III)}$$

$$\frac{1}{2} \begin{pmatrix} H_{11} & H_{12} & H_{13} \\ H_{21} & H_{22} & H_{23} \end{pmatrix} \begin{pmatrix} dC^2 \\ 2dCdT \\ dT^2 \end{pmatrix} + (O(3))$$

In the Taylor expansion, the first term comprises values of the signals S1 and S2 exactly at a selected $CO_2$-concentration C0 and in a gas mixture T0=0; the second term reflects in a first order how the signals S1 and S2 change if the concentration C or the composition of a gas mixture, i.e. the linewidth T, is changed slightly or by the amount of dC and dT. The coefficient matrix for corrections of the first order is termed as a Jacobian matrix J. The third term comprises a correction caused the changes in a second order, etc. A coefficient matrix H appearing in the second order contains the second derivatives of signals S1 and S2, etc. Generally, the first order is already sufficient for reaching a sufficient determination accuracy and neither in terms of mathematical methods is it necessary to deal with changes of the second order. The matrix J representing signal derivatives is commonly used in iterative calculation methods. The calibration sequence of the novel measuring method can be based on the determination of this Jacobian matrix, since the correction caused by the broadening of a line on the $CO_2$-concentration is always sufficiently small (even in an $N_2O$-mixture typically less than 10% of the uncorrected $CO_2$-concentration).

Determination of a Jacobian matrix and the entire calibration sequence are implemented as follows:

1) The signals S1 and S2 are measured over the entire measuring range, i.e. 0–10%, of carbon dioxide or a sample gas Gt in general by using a selected nominal gas mixture (e.g. $CO_2$ in nitrogen gas). The result is S1=S1(C,T=0) and S2 =S2(C,T=0).

2) These curves are used for calculating the signal derivatives $$\frac{\partial S_1(C, T0)}{\partial C} \quad \frac{\partial S_2(C, T0)}{\partial C}$$

relative to the $CO_2$-concentration. The derivatives are calculated at a point (C,T0).

3) The entire $CO_2$ concentration range is used for selecting therefrom preferably 3–5 concentration levels (C1) used for varying a background gas mixture to change the collision broadening by the amount of dT. These levels can be e.g. 2.5%, 5%, 7.5%, and 10% $CO_2$. Different collision broadening values are obtained by admixing in a background gas ($N_2$) e.g. nitrous oxide ($N_2O$). In this context, it should be noted that the selection of a mixing gas bears no significance as the measuring system is selected to be such that the gas only influences a measuring signal through collision broadening and the novel measuring method of the invention is totally indifferent as to how the broadening of the absorption line of a $CO_2$-molecule has been accomplished. Hence, neither does the actual concentration measurement require any information about what has caused the line broadening.

4) Determination of derivatives from measurements of the preceding sequence (3)

$$\frac{\partial S_1(C1, T)}{\partial T} \quad \frac{\partial S_2(C1, T)}{\partial T}$$

These are hence calculated at points (C1,T0).

5) For a maximal determination accuracy it is possible to use several $CO_2$-levels and the interlevel values can be interpolated to $CO_2$-concentrations other than those used in calibration.

The calibration procedure shall now be further described in reference to FIG. 7. This illustrates an indicator, whose horizontal axis depicts a normalized path length, i.e. a distance from a light source at a given $CO_2$-concentration, which is the same as the attenuation of a signal S1 as a function of the concentration C when the detector position (i=1.2) is maintained constant. Thus, the derivative of the indicator can be used for obtaining the derivatives needed in the calibration sequence. On the other hand, by studying how the signal changes (corresponding to the direction of transmission axis) whenever the normalized path length and the $CO_2$-concentration are constant C1 (LC=constant) and the linewidth T changes, it is possible to obtain derivatives needed in the calibration sequence 4. Thus, the calibration involves measuring the information of FIG. 7 for two detectors set at different path lengths LC and these are used for calculating a required Jacobian matrix as a function of the $CO_2$-concentration for a nominal gas mixture, which has a normalized T=0.

It was pointed out above that, instead of the signal S1, it is preferable to use the ratio S1/S2 between the signals S2 and S1. The calibration procedure in terms of this selection is similar and comprises sequences 1–5 with the exception that S1 is replaced with the signal S1/S2 (thus, in this case, a Taylor expansion is applied to signal S2 and ratio S1/S2). The Jacobian matrix of this selection can be determined e.g. on the basis of experimental measuring information as shown in FIGS. 8A and 8B.

In the subsequent sequence (storage of calibration data) of the novel measuring method, the acquired calibration data is stored e.g. in a memory devices, from which it can be delivered to a measuring device for use in the calculation sequence of the measuring method. The calibration data contained in a storage instrument may in a preferred case include e.g. the behavior of signals S2 and S1/S2 in a nominal gas mixture (having a normalized T=0) as a function of the $CO_2$-concentration C and, in addition, a Jacobian matrix J or most preferably an inverted matrix $J^{-1}$ of J. The storage instrument may also contain other calibration-related and other information, such as corrections caused by temperature or an external pressure, sensor identification data, etc.

In the measuring sequence of the novel method, i.e. during the course of an actual measurement or analysis following the calibration, an unknown gas mixture is first supplied into a measuring chamber from a chamber inlet duct e.g. by means of continuous pumping, the gas mixture discharging as a continuous flow through an outlet duct. The measuring chamber is illuminated throughout with a light source and detectors are used to measure the signals S1 and S2. The null signal levels or the signals in the event that the measuring chamber is supplied with air or some other neutral gas mixture can be determined as a separate measuring sequence. The actual signals during the course of a measuring sequence are normalized to the null or zero signals. The adjustment to zero can be effected according to timing controlled by a given regular microprocessor. The measuring operation will be described in more detail hereinafter in the context of introducing preferred embodiments of the invention.

The final sequence in the novel invention is a calculation sequence, which involves the actual determination of the $CO_2$-concentration C and the collision broadening T by means of a selected mathematical method. As pointed out above, the selection of a mathematical method is related to the selected calibration method. One preferred solution in this context involves two mathematical methods, which apply the above-described Jacobian matrix J. Other mathematical methods can be applied as well. In a preferred calculation sequence of the novel method, mathematical methods are applied to the signals S2 and S1/S2 for obtaining a concentration measuring result M.

If the expectable correction caused by collision broadening is insignificant (e.g. measuring carbon dioxide in a mixture of nitrogen and oxygen), a Taylor expansion for the signals can be used for simply working out the correction dC (C=C0+dC) and the collision broadening dT (T=T0+dT=dT). The expansion (I) yields in a first order:

$$\begin{pmatrix} dC \\ dT \end{pmatrix} = \begin{pmatrix} \frac{\partial S_1(C0, T0)}{\partial C} & \frac{\partial S_1(C0, T0)}{\partial T} \\ \frac{\partial S_2(C0, T0)}{\partial C} & \frac{\partial S_2(C0, T0)}{\partial T} \end{pmatrix}^{-1} \begin{pmatrix} S_1 - S_1(C0, T0) \\ S_1 - S_2(C0, T0) \end{pmatrix} \quad (IV)$$

wherein $(\ )^{-1}$ is an inverted matrix of the Jacobian matrix determined in a gas mixture, in which T=0 and C=C0 and C0 is calculated e.g. from the signal S1, whereby S1=S1 (C0, T=0) and S2(C0,T=0) is determined on the basis of calibration data in a nominal gas mixture. S1 and S2 are measured signals in an unknown gas mixture. This method is the simplest one and, thus, it determines first an estimate calculated solely from the signal S1 or S2 regarding the $CO_2$-concentration and then corrects this result by means of the other signal S2 or S1 and the Jacobian matrix.

If the collision broadening is large, the above-discussed simple calculation does not yield a sufficiently accurate result. In this case, it is possible to apply iterative methods, e.g. a so-called Newton method, the detailed description of which can be found in textbooks dealing with mathematical methods. Briefly and simply, the Newton method is a continuation of the preceding (Taylor serial expansion) method, such that the corrections dC and dT are continuously exacted by repeating iteratively the above-described process. Preliminary corrections dC(1) and dT(1) obtained from cycle 1 are used for calculating new arguments or C(2)=C0+dC(1), T(2)=dT(1). These argument values are used for determining new estimates for the signal S1(n=2)=S1(C(2),T(2)) and S2(n=2)=S2(C(2),T(2)), followed by the determination of deviations S1—S1(n=2) and S2—S2(n=2), which are used for calculating new corrections dC(3) and dT(3), etc. In the method, n symbolizes iteration cycles. This is continued until reaching a sufficient predetermined accuracy and a final concentration Cf for a gas component, such as carbon dioxide, as a concentration measuring result M.

In addition to the above-described measurement of collision broadening, it is also possible to measure an additional signal, i.e. a third signal S3, through an above-discussed, per se known band rejection filter. Hence, this third signal is obtained from a beam which has traveled through a measuring chamber and an optical bandpass filter as well as through an optical band rejection filter, such as a gas filter. In this case, the transmission of an optical band rejection filter is substantially lower than the transmission of a filter intended for obtaining the above-described second signal S2. Otherwise the filters are of the same type, i.e. containing that gas component or a mixture of that gas component whose concentration is to be determined during the course of an actual measurement. For the signal S3, the measuring length LC is longer or the concentration of a gas component is higher. In this case, the measuring method can be expressed mathematically as a solution to the following non-linear cluster of equations:

$$\begin{pmatrix} S1 \\ S2 \\ S3 \end{pmatrix} = \begin{pmatrix} A_{11}(S1, S2, S3) & A_{12}(S1, S2, S3) \\ A_{21}(S1, S2, S3) & A_{22}(S1, S2, S3) \\ A_{31}(S1, S2, S3) & A_{32}(S1, S2, S3) \end{pmatrix} \begin{pmatrix} C \\ dT \end{pmatrix} \quad (V)$$

This cluster of equations is solved analogically with the above-described solution which applied a simpler matrix. Since the cluster of equations is symmetrical in terms of all variables, it makes actually no difference which beam, after passing through the measuring chamber and producing a given signal, will be regarded as a beam producing whichever of the signals S1 or S2 or respectively the signals S1 or S2 or S3. For the sake of clarity, however, in this application the signal S1 is used to represent a signal corresponding to the lowest absorption and the signal S2 as one corresponding to a higher absorption and the signal S3 as one corresponding to the highest absorption.

Especially in the case of the above-discussed three signals S1, S2, S3, the advantage is that, if necessary, a measuring sensor, from which these signals are obtained, can be used for example over an extensive concentration range of a gas component to be measured, such as $CO_2$, by effecting the calculation with just two of these three signals. If for example, the concentration of carbon dioxide is high, use is made of the signals S1 and S2 obtained in the closest vicinity of a radiation source and possibly, if necessary as stated above, the signal S3 for eliminating errors resulting from disturbance factors other than collision broadening. Thus, the absorption length LC is brought at least close to the optimum, as described above. If on the other hand, the concentration of e.g. carbon dioxide is low, it is possible to use the signals S2 and S3, obtained furthest away from a radiation source, as signals S1' and S2' corresponding to the signals described above in connection with the calculation. Thus, the absorption length LC is also brought close to the optimum, as described above.

We have thus described a novel method of the invention. The sensor applications, which fall within the scope of the novel invention, are not limited to the use of just a single long analysis chamber or to a single analysis chamber provided with parallel ducts, although those are advantageous. We shall subsequently study various sensor designs according to the principles of the invention. As far as these are concerned, it should be appreciated that the applied definition "absorption length" L1, L2, L3 refers to a physical or mechanical length, which is not the same thing as the length LC used previously in this specification, the latter being a product of the mechanical absorption length and the concentration.

Figure 9A:
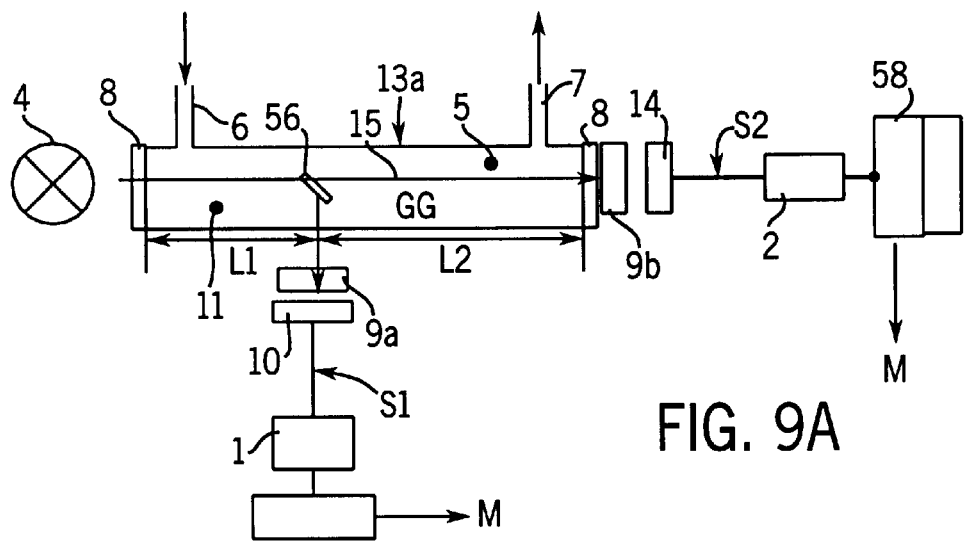
FIG. 9A shows a first preferred embodiment for a device of the invention. This embodiment makes use of a single long analyzing chamber, wherein detectors set at two different lengths measure radiation quantities absorbed over said radiation path lengths. This results in two linearly independent signals S1 and S2, which have a mutual relationship and which are used, according to the invention, to determine both the $CO_2$-concentration and a parameter indicative of collision broadening.
Figure 9B:
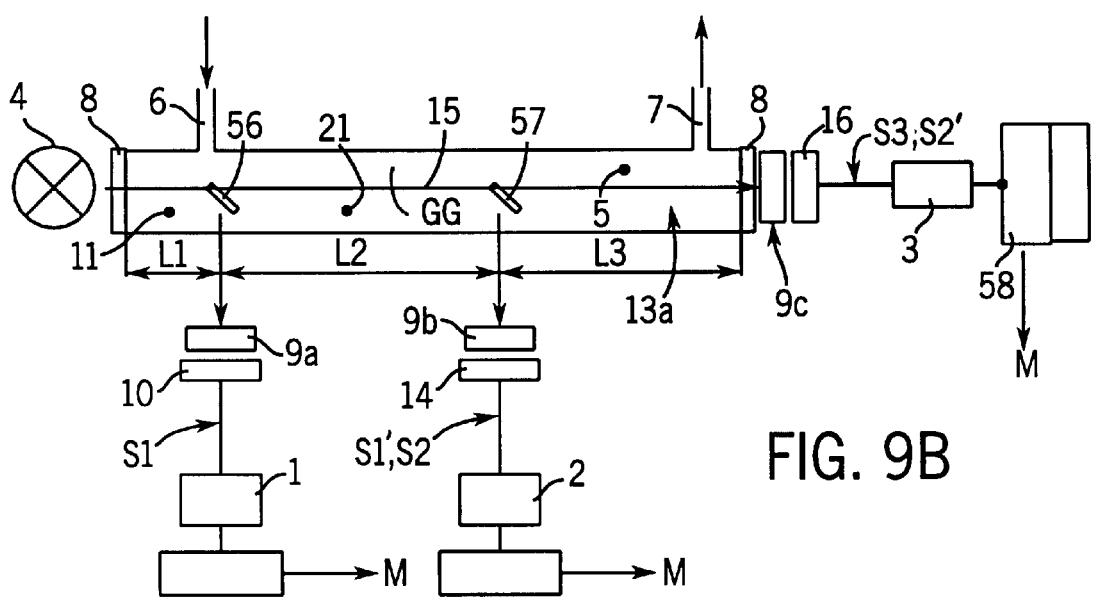
FIG. 9B shows a second preferred embodiment for a device of the invention. This embodiment makes use of a single long analyzing chamber, wherein detectors set at three different lengths measure radiation quantities absorbed over said radiation path lengths. This results in two linearly independent signals S1 and S2, which have a mutual relationship, and a third signal S3 or, depending on the concentration of a gas component to be measured, two more linearly independent signals S1' and S2', which have a mutual relationship and which are used, according to the invention, to determine both the $CO_2$-concentration and a parameter indicative of collision broadening.

FIGS. 9A and 9B illustrate the most typical and beneficial design for a sensor device of the invention. In this configuration, the gas mixture to be measured is supplied into a long analysis chamber 13a from a sample-gas inlet tube 6 and discharged from an outlet tube 7. The measuring system includes two detectors 10 and 14 for producing an electrical signal S1 and S2 in two separate data channels 1 and 2, one of which measures the signal of a radiation source 4 at a long path length from the end of the analysis chamber 13a and by way of a first element, e.g. a semi-transmissive mirror 56, mounted inside the chamber and deflecting aside some of radiation 15. The deflecting or diverting element 56 is positioned such that the radiation advances a different path length in the sample gas mixture prior to reaching the detectors 10 and 14 through an appropriate optical bandpass filter 9. Thus, the measuring chamber extending to the detector 10 has a mechanical absorption length L1 which is shorter than an effective total absorption length L1+L2 to the second detector resulting from an absorption length L2 of the rest of the analysis chamber 13a. Both absorption lengths L1 and L2 contain an identical gas mixture GG, constituted by the very gas mixture which is to be measured for the concentration of a given gas component Gm. The deflecting element is preferably positioned as described in the method section, whereby a sample chamber for the signal S2 is formed between an end 8 of the analysis chamber facing away from the radiation source 4 and the deflecting element 56. The absorption length L1 extending between the deflecting element 56 and an end 8 of the analysis chamber facing towards the radiation source 4 constitutes for the signal S2 an optical gas filter 11, featuring the characteristics of the invention. The transmission bands of optical bandpass filters 9a and 9b are located in alignment with the absorption line of a gas to be measured in such manner that other gases of the gas mixture do not absorb within this range at least to a harmful extent. If the question is about carbon dioxide, this range has its mid-point at the wavelength of 4.26 mm and a half-value width of about 100 nm. This range accommodates, as pointed out above, about 80 narrow absorption lines. Both ends 8 of the chamber and the chamber wall along the optical path of the detector 10 are fitted with windows transmissive to radiation. The radiation source 4 is common to both measuring ducts S1 and S2, so that fluctuations in the radiation would be the same in both ducts.

The sensor design of FIG. 9B includes an additional second deflecting element 57 for deflecting, after the mechanical second absorption length L2 downstream of the first absorption length L1, some of a beam 15 aside to the detector 14 for obtaining the second signal S2. Downstream of the second deflecting element 57, the analysis chamber 13a includes a further mechanical third absorption length L3, followed by a detector 16, the beam falling thereon by way of an optical bandpass filter 9c. This third absorption length constitutes a sample chamber 5 for the signal S3 and, on the other hand, the second absorption length L2 constitutes a second optical gas filter 21, which is in series with the first optical gas filter 11. The second gas filter 21 may feature the above-described characteristics of the invention and/or the characteristics of a per se known band rejection filter or something therebetween. In terms of its transmission distribution of wavelength, the employed bandpass filter 9c is of the same type as the above-described filters 9a and 9b. The detector 16 is connected to a third data channel 3 and a third signal S3 is obtained therefrom. Both presently discussed deflecting elements 56 and/or 57 can be semi-transmissive mirrors, some of the beam 15 arriving thereat reflecting out of the analysis chamber and some of it continuing on within the analysis chamber. It is also possible to employ mirrors so small in terms of the reflective area thereof that some of the beam passes by the mirror surface. This can be effected e.g. with stripe-mirrored surfaces, whereby the elements 56 and 57 can be provided with stripes extending crosswise and e.g. perpendicularly to each other. The mirror surface must of course be provided with a base transmissive to the applied radiation. In the sensor designs of FIGS. 9A and 9B, the measuring chamber 5, the first optical gas filter 11, and the possible second optical gas filter 21 are in a flow communication with each other, the same gas mixture GG to be analyzed flowing in all of them.

In the sensor design of FIGS. 9A and 9B, the optical paths and the lengths thereof for radiation falling on the detectors are dimensioned as described earlier in this specification in reference to the method of the invention. If the measuring chamber contains a $CO_2$-concentration which is low, the primary $CO_2$-signal S2 is measured down a long optical path, i.e. by means of the detector 14. When the $CO_2$-concentration is high or close to the highest value of the entire measuring range, the primary measuring signal S1 may be constituted by radiation measured by the detector 10. The other signal S1, and respectively S2, is used for producing a quantity representative of collision broadening, as described in the method section of the invention. In the event that the sensor, as shown in FIG. 9B, is provided with three detectors 10, 14 and 16, the concentration analysis of a gas component can be effected by using all of these, with three different signals S1, S2 and S3 available. The third signal can be used for correcting error sources other than those resulting from collision broadening. Depending on the concentration of a gas component to be measured, such as carbon dioxide, with respect to the size of an analysis chamber and the calibrating concentrations, it is also possible to use any two of these three signals. If, for example, the $CO_2$-concentration is low, the primary signal may be considered to be a signal S2(=S1') obtained from the detector 14 and the collision broadening can be calculated by using e.g. a signal S3(=S2') obtained from the detector 16, as described above. When the $CO_2$-concentration is high or close to the highest value of the entire measuring range, the primary measuring signal S1 can be constituted by radiation measured by the detector 10 and the collision broadening can be determined on the basis of the second signal S2 obtained from the detector 14. On the other hand, with an extremely low $CO_2$-concentration, it is possible to use the signal S3 obtained from the detector 16 as a primary signal S1'. Any other combination may be useful just as well.

Figure 10A:
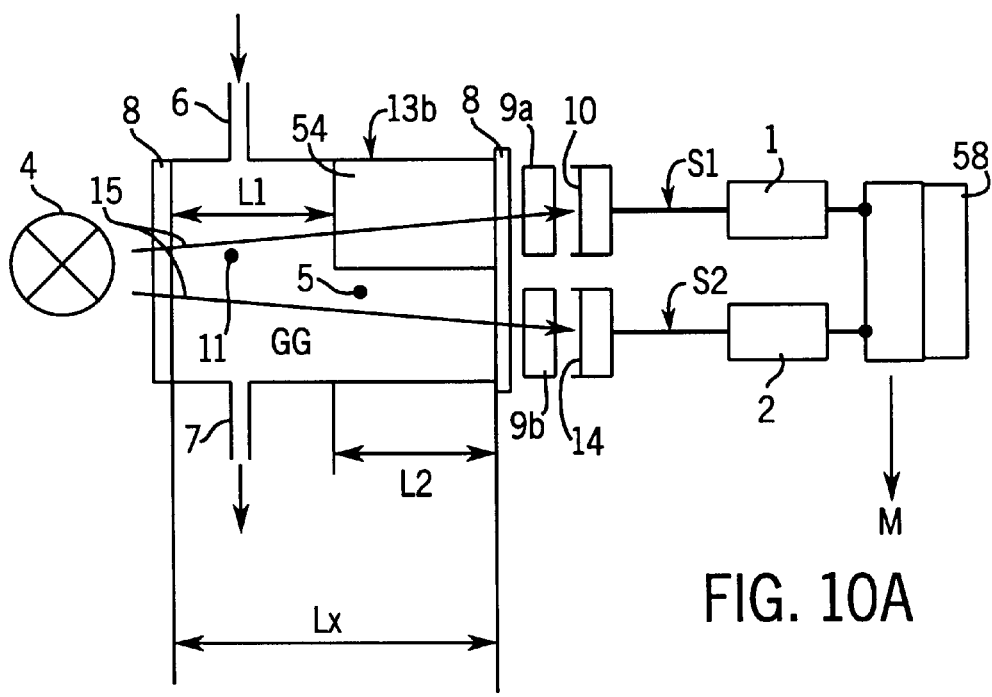
FIG. 10A shows a third preferred embodiment for a device of the invention. In this embodiment, two different linearly independent signals S1 and S2, which have a mutual relationship, are produced over two different radiation path lengths by fitting one analyzing chamber with an element transmissive to radiation and diverting the gas mixture to be measured in order to reduce the length of a first measuring conduit or duct for producing the signal S1. The other signal S2 is obtained from a duct or conduit with no diverting element. According to the invention, the signals are used for calculating both the $CO_2$-concentration and a parameter indicative of collision broadening.

FIG. 10A illustrates another fundamental way of providing two optical paths of an unequal length in a single continuous analysis chamber 13b. In this case, the mechanical absorption length of a data channel 1 (S1) is given a length L1 by reducing a length Lx of the chamber with a diverting element 54, which is mounted in the measuring chamber on the path of radiation falling on this data channel. The diverting element is made of a material which is as highly transmissive to the applied wavelengths as possible and preferably without effects on the intensity distribution of a radiation spectrum. This element may be e.g. a sapphire or $CaF_2$ rod or another material which is highly transmissive to radiation, in the case of carbon dioxide within the range of 4.3 μm. The element reducing the length of an optical path may also be e.g. an air-filled chamber, provided with optically transmissive windows. Thus, the diverting element 54 provides the analysis chamber with the absorption length L1 and a measuring chamber 5. In this case, a sub-length L2 of the analysis chamber, corresponding to the length of the diverting element, creates together with the length of the measuring chamber a second absorption length L1–L2. A section of the data channel 2 equal to the first absorption length L1 constitutes an optical gas filter 11 for a signal S2. A beam 15, after passing through the measuring chamber 5 and the diverting element 54, continues further through an optical bandpass filter 9a and on to a detector 10 and a beam 15, after passing through the gas filter 11, continues further through an optical bandpass filter 9b and on to a detector 14. The first detector 10 delivers a first signal S1 and the second detector 14 a second signal S2. The length Lx of the analysis chamber and the length L1 of the diverting element are designed such that the gas filter 11 features the characteristics of the invention. In this case, the optical bandpass filter may also be constituted not only by two separate identical filters, as shown in the figures, but also by a single filter, with beams of both data channels 1 and 2 passing therethrough. Preferably, the optical bandpass filter has a transmission band which is exactly the same in both optical paths and, in addition, its band is selected in such a manner that other measurement disturbing gases do not have a direct effect on the measurement of a gas component, such as carbon dioxide.

Figure 10B:
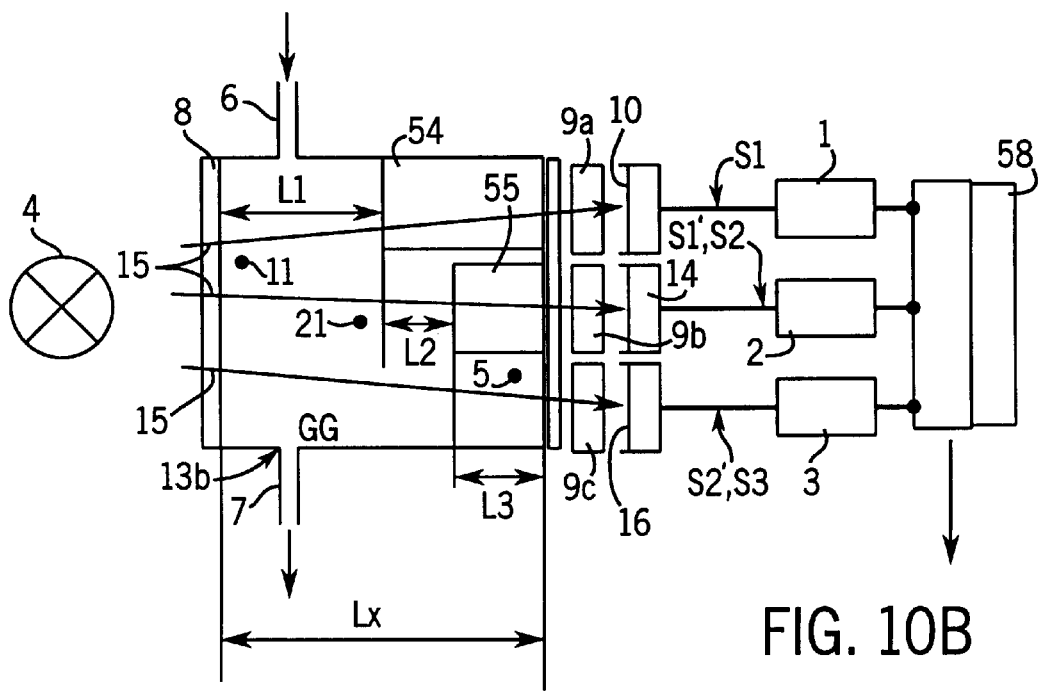
FIG. 10B shows a fourth preferred embodiment for a device of the invention. This embodiment involves the production of at least two different linearly independent signals S1 and S2, which have a mutual relationship, and a third signal S3 or, depending on the concentration of a gas component to be measured, two more linearly independent signals S1' and S2', which have a mutual relationship. Two signals are obtained over two different radiation path lengths by fitting one analyzing chamber with an element transmissive to radiation and diverting the gas mixture to be measured in order to reduce the length of a first measuring duct for producing the signal S1. In addition, this one analyzing chamber is provided with a second element transmissive to radiation and diverting the gas mixture to be measured in order to reduce the length of a second measuring duct for producing the above-mentioned third signal S2 or respectively S1'. The third signal S3 or, respectively, the second signal S2' is obtained from a duct with no diverting element. According to the invention, the signals are used for calculating both the $CO_2$-concentration and a parameter indicative of collision broadening.

FIG. 10B depicts a modification of the embodiment shown in FIG. 10A. In this solution, the analysis chamber 13b includes even a second diverting element 55, whereby the chamber is also provided with a third absorption length L1+L2+L3 by reducing the length Lx of the entire chamber with a length L3 corresponding to the second diverting element. Radiation 15, having passed through this third absorption length and still continuing through a third optical bandpass filter 9c, is received with a third detector 16 for producing a third signal S3 in the third data channel 3. This third absorption length constitutes a measuring chamber 5, and the second absorption length L2 constitutes an optical gas filter 21, and the first absorption length L1 constitutes an optical gas filter 11 for the signal S3. The gas filters 11 and 21 feature the above-described characteristics of the invention and/or the characteristics of a per se known band rejection filter. In terms of its transmission distribution of wavelength, the employed bandpass filter 9c is of the same type as the above-discussed filters 9a and 9b and it may be constituted by a given point of the same filter, as explained in reference to FIG. 10A.

In the cases of FIGS. 9B and 10B, the measuring chamber 5, the first optical gas filter 11, and the possible second optical gas filter 21 are also in a flow communication with each other, the same gas mixture GG to be analyzed flowing in all of them. The gas component to be measured arrives in the analysis chamber 13b by way of a flow tube 6 and discharges through a flow tube 7. According to the concentration of a gas component, such as $CO_2$, to be measured, these embodiments may also be provided with all three signals S1, S2, S3 or any two of said three signals, exactly as described in reference to the embodiments of FIGS. 9A and 10A. These can be used for producing respective signals S1' and S2'. With respect to the embodiments of FIGS. 9B and 10B, the result of this possibility is that the previously ascertained signal ratios apply no matter which one of the signals is used, i.e. the signal S2 or S3 of a detector furthest away from a light source at the top of concentration is no more than about 60%, preferably no more than about 40%, and typically 5%–30% of what it is at the same location on the bottom threshold of the concentration range and at the same time the detector closest to a radiation source is located such that, in the middle of the concentration range, the signal S1 is 95%–50% and typically 90%–70% of what it is at the very bottom of the concentration range, close to a radiation source 4.

Thus, it is characteristic of the sensor designs shown in FIGS. 9A–10B that both detectors 10 and 14 or all detectors 10, 14, 16 measure through the same sample gas mixture at different path lengths. In this context, there were shown two different ways of varying the distance traveled by radiation in a sample gas mixture. Even if this principle is applied, the invention is not limited to these embodiments but encompasses other ways of providing two or more different absorption lengths. One such way would be to guide the radiation to travel through an analysis chamber several times by means of mirror surfaces for producing e.g. a signal S2 and in such a manner that the radiation passes e.g. just once through an analysis chamber for producing a signal S1. Another higher number of passes through an analysis chamber could then produce a signal S3. The number of radiation passes through an analysis chamber for signals S2 and S3 could be two to five times and e.g. along approximately the same optical path. These embodiments, wherein various signals S1, S2 and possibly S3 are extracted from a beam which has traveled over various absorption lengths and hence also various path lengths LC inexplicitly in a sample gas GG (the optical gas filters 11 and 21 thus being filled with a gas mixture to be examined), have a particular advantage in that all gases, through which the beams 15 used in a measurement are traveling, are exactly at the same temperature and pressure. This is a way of avoiding measuring errors, which otherwise would have to be corrected by various actions.

Figure 11A:
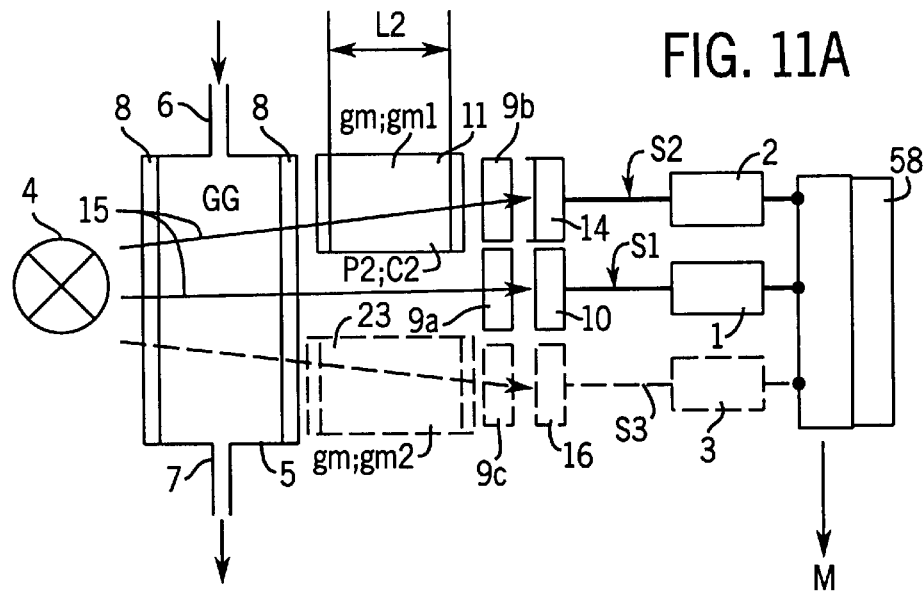
FIGS. 11A, 11B, 11C and 11D show a fifth and sixth as well as a seventh and eighth embodiment for a device of the invention. A typical feature in these devices is that the effective optical path length covered by radiation is regulated by means of a stationary gas-filled band rejection filter. In the fifth (FIG. 11A,), seventh (FIG. 11B) and eighth (FIG. 11C) embodiment of the device, the band rejection filter and the measuring chamber are dimensioned in a preferred fashion according to the invention by producing two linearly independent signals S1 and S2, which have a mutual relationship.
Figure 11B:
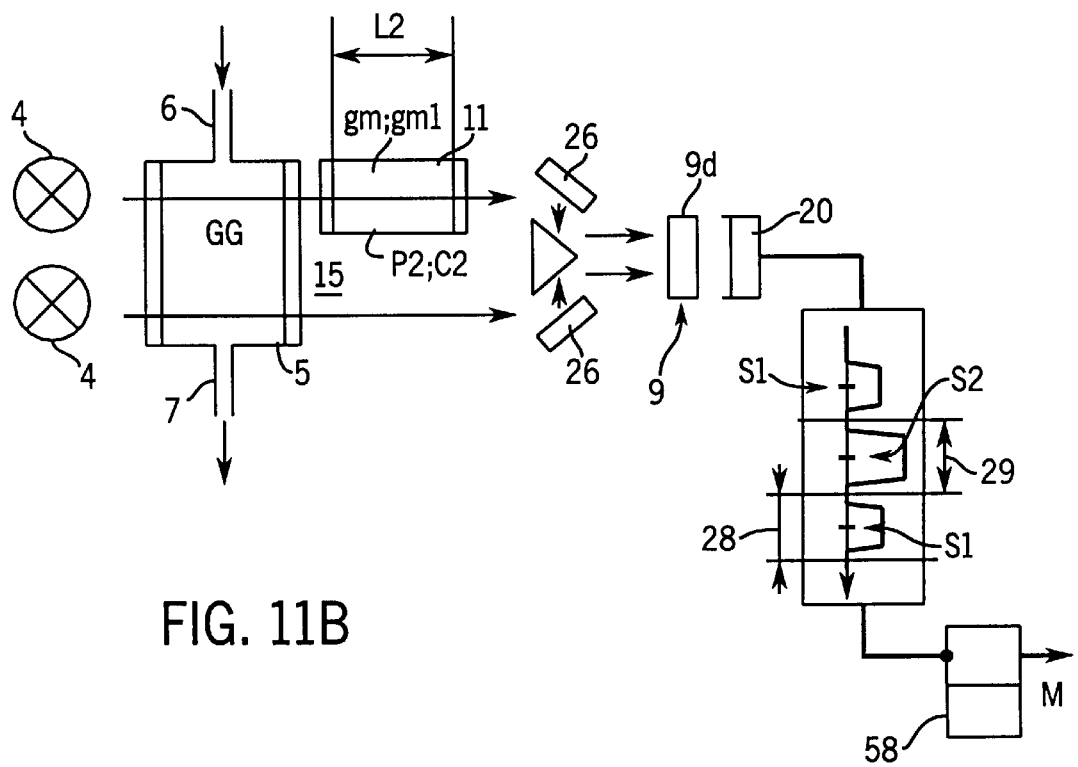
Figure 11C:
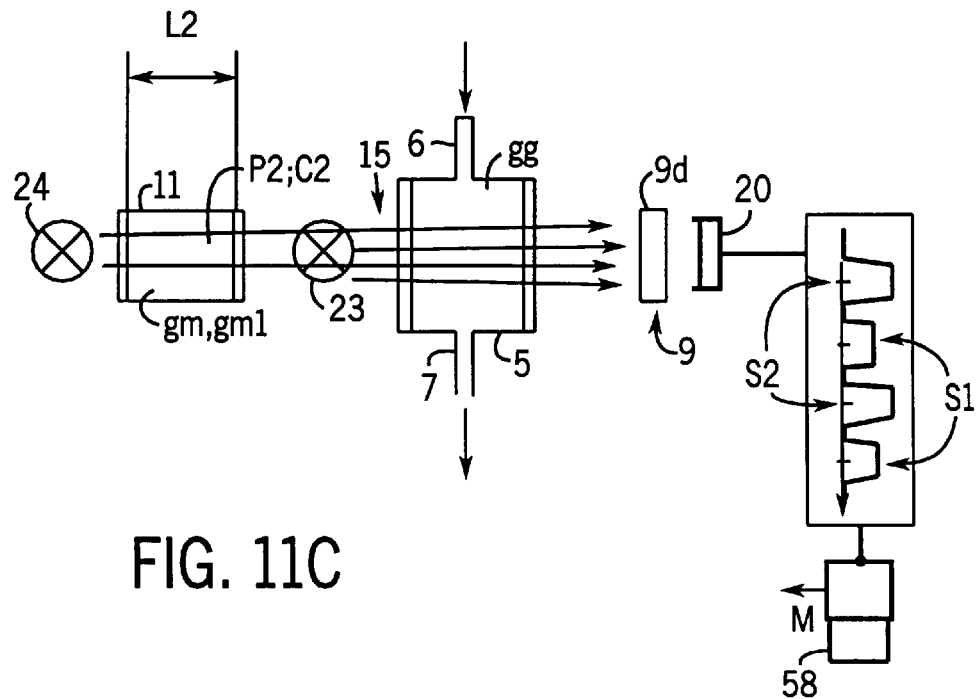

FIGS. 11A, 11B and 11C show three different designs for a sensor device within the scope of the invention. In a conventional manner, a radiation source 4 emits radiation 15 through a measuring chamber 5 and further by way of an optical bandpass filter 9a to a detector 10, from which is obtained a first signal S1. The gas mixture to be examined arrives through a flow tube 6 only into the measuring chamber 5 and discharges therefrom through a flow tube 7. These measuring systems are further provided with a sealed, i.e. invariable optical gas filter 11, wherein the amount of a gas component Gm to be measured is preset to conform with the invention either by means of its pressure P2 and/or absorption length L2 or alternatively by means of a gas component mixture $Gm_1$ and its pressure P2 and/or absorption length L2 and/or concentration C2. This chamber is only set in a second optical radiation path extending through a second bandpass filter 9b for producing a second signal S2 therefrom by means of a detector 14. If necessary, the pressure of a gas in the chamber can be other than a normal pressure and the gas may also be a mixture gas containing the type of gas to be measured. The gas vessel 11 functions as an optical filter, which filters radiation in an amount determined in the invention at the peaks of the absorption lines of a gas contained in the vessel. It is characteristic of the embodiments shown in FIGS. 11A–12 that the magnitude of a second signal S2 is determined to be 50%–95% and preferably 70%–90% of the first signal S1 or, alternatively, the magnitude of a first signal S1 is determined to be 200%–105% and preferably 140%–110% of the second signal S2. The gas filter 11 is penetrated by radiation, which is alongside the peaks of the absorption lines and has an almost unobstructed access to the detector 14. Thus, the detector 14 is incapable of detecting or detects more poorly a similar type of gas contained in the sample chamber 5, since the radiation at the absorption peaks of said gas has been filtered at least partially in the vessel 11. Hence, such a vessel added in an optical path increases the effective optical passage of radiation in a sample gas mixture in such a manner that a method of the invention can be used for calculating therefrom an exacted gas concentration regardless of a mixture gas. Its function can be conceived the same way as in the solutions shown in FIGS. 9A–10B, which only differ from the designs of FIGS. 11A–11C in that there is no separate pre-sealed vessel but the sample gas itself serves as a pre- or after-filtering element. As for the embodiments of FIGS. 11A–11C, if the gas Gm of the gas filter 11 or the composition of its mixture $Gm_1$ and/or the other above-discussed quantities are selected appropriately e.g. in such a manner that the absorption lines of radiation transmitted through the vessel has a width which is close to that of the absorption lines of a gas component to be measured in a no collision-broadened state, the signal S2 will indicate effectively the collision broadening of also a gas to be measured and contained in the sample chamber 5. Thus, the signal S2 of the detector 14, together with the signal S1 of the detector 10, contains information both about the collision broadening of a gas to be measured and about its concentration the same way as described above in reference to a method of the invention.

Figure 11D:
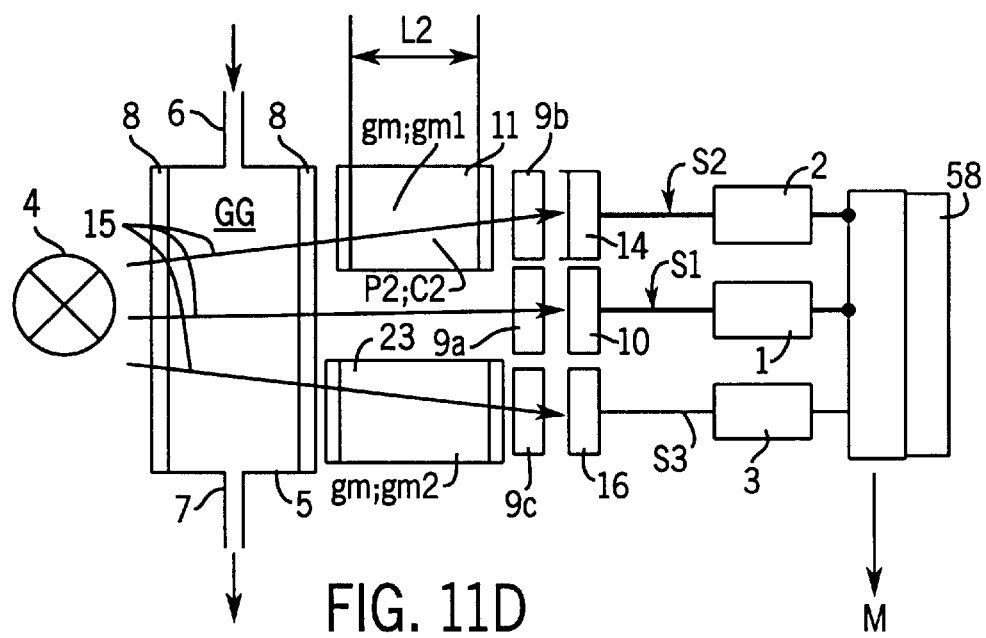

In FIG. 11A, the above-described assembly is shown the same way as in FIGS. 11B and 11C. In addition, FIG. 11D illustrates a second optical gas filter 23, which is constituted by a sealed chamber and which also contains a gas component Gm to be examined or a mixture $Gm_2$ thereof. Some of radiation 15 passes through this gas filter and further by way of an optical bandpass filter 9c to a third detector 16, from which is obtained a third signal S3 in a third data channel 3. This gas filter has an absorption length and/or a pressure and/or a gas component concentration which are different from those found in the first gas filter 11. The second gas filter may be of the same type as per se known powerful band rejection filters, as described above. The signals S1, S2, S3 can be used as previously explained in this specification.

FIGS. 11B and 11C illustrate in principle a solution similar to that shown in FIG. 11A. Unlike FIG. 11A, which shows the use of two detectors and a single radiation source, the solutions of FIGS. 11B and 11C employ a single optical bandpass filter 9d and a single detector 20 as well as two radiation sources 4. In the assembly of FIG. 11B, the signals of various radiation sources are combined by means of a mirror assembly 26 connecting the optical paths. In the assembly of FIG. 11C, the radiation sources are arranged successively, such that a gas-filled band rejection filter 11 lies between the sources. This arrangement offers a remarkable advantage, since the optical path penetrated by a measuring chamber 5 is exactly the same and thus common to both ducts. Hence, for example, the dirt accumulating on the windows of a sample chamber does not interfere with the determination of carbon dioxide concentration. Since there is just one detector 20 available, the signals S1 and S2 of measuring data channels 1 and 2 must be time-multiplied in such a manner that, at a moment $t_1$, just one of the radiation sources 4 is kept on and this is switched off at a moment $t_2$ when, on the other hand, just the other one of the radiation sources 4 is maintained on. Thus, the measurement is carried out by pulsing the radiation sources alternately for producing two separate measuring cycles 28 and 29, one 28 for the first signal S1 and the other 29 for the second signal S2.

Figure 12:
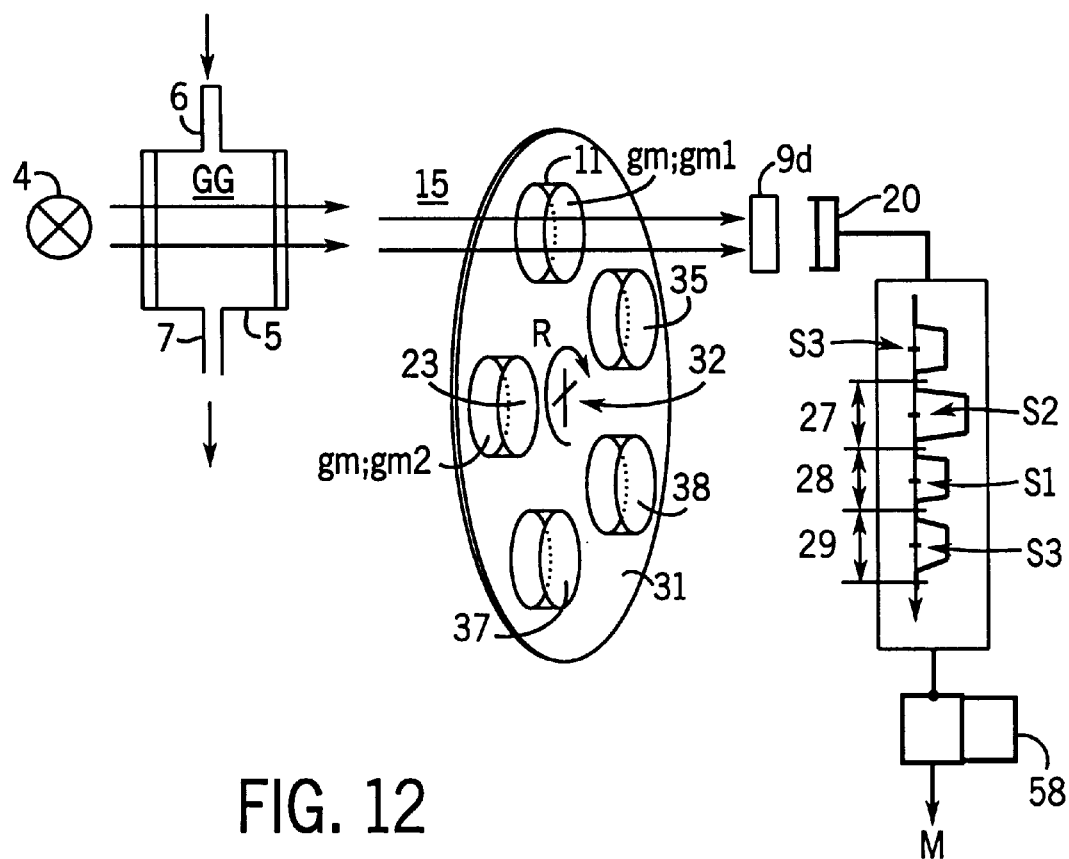
FIG. 12 shows a ninth embodiment for a device of the invention, which only employs a single detector and a single radiation source. The effective path length covered by radiation in the measuring chamber is regulated by means of optical gas-filled band rejection filters mounted on a rotating disc. As the disc is rotating, there develops at least two linearly independent signals S1 and S2 etc., which have a mutual relationship, as well as, if desired, also a third signal S3, which are used according to a method of the invention for determining the $CO_2$-concentration and a parameter indicative of collision broadening.

FIG. 12 shows another sensor design, which employs just a single detector 20 and a single radiation source 4. This is possible since the effective optical passage of radiation is regulated by means of optical gas-filled band rejection filters 11, 23, 35, 37, 38 mounted on a disc 31 rotating R around an axial line 32. The disc 31 must be provided with at least two different gas-filled band rejection filters. One of these, e.g. a filter 35, can be non-absorbing and thus a mere aperture or an air-filled vessel. On the other hand, the other one of these is an optical gas filter 11 of the above-described invention, which in this case is constituted by a sealed vessel the same way as in the embodiments of FIGS. 11A–11C. Thus, the gas filter 11 contains either a gas component Gm or a first mixture $Gm_1$ thereof. Furthermore, the absorption length and/or internal pressure of a gas component and/or the concentration of a gas component are selected in accordance with the invention. Rotation of the disc produces the measuring cycles 28 and 29 and a first signal S1 and a second signal S2 therefor. In addition, the rotating disc can be fitted with a second optical gas filter 23, which is also a sealed chamber and contains a gas component Gm or a second mixture $Gm_2$ thereof for obtaining a third signal S3. This third signal S creates a third cycle 27. The rotating disc 31 can also be provided with other optical band rejection or bandpass filters, which may improve the determination accuracy of carbon dioxide by operating over the same spectral band as the filter 11, but they can also operate over another spectral band, in which case they are primarily intended for determining the concentration of other gas components present in a gas mixture.

It is also within the spirit of this invention that the spectral transmission of a band rejection filter 11 is known accurately and that the information contained therein is stored for example in a memory element 58. Such spectral information may include for example the effective length of a band rejection filter determined mathematically as a function of a $CO_2$-concentration for each gas concentration of a measuring chamber. Thus, it is possible to mathematically apply the same analysis as that set forth in the description of a method of the invention. Hence, the measuring systems of FIGS. 11A–11C and 12 are effectively reverted to using two preferred measuring lengths in a substantially single long chamber.

It is obvious for an expert that the measuring systems set forth thus far are not the only possible systems that a method of the invention can be applied to. The number of radiation sources and detectors can be varied, likewise the gas-filled band rejection filters can be mounted either upstream or downstream of a measuring chamber, the number of measuring data channel can be higher than two or three, which cases have been described above, etc. Three data channels 1, 2 and 3 and three signals S1, S2 and S3 are needed in a situation which requires an accurate $CO_2$-measurement even if the sensor is soiled or in which the measurement may be disturbed e.g. as a result of excessive moisture or the like.

When measuring a plurality of gas components, it is possible in accordance with the invention to employ a measuring system, wherein a per se conventional multi-component gas analyzer is provided with a collision-broadening measuring duct according to a method of this invention for just one gas component, such as e.g. carbon dioxide, to be measured. The measurement of collision broadening implemented by means of this special duct can be used for offsetting the effect of a collision broadening on the measuring results of also all other gas components, i.e. the multi-component analysis can be made considerably more accurate by implementing the measurement of a collision broadening by means of just a single duct. Naturally, the measurement of a collision broadening can be carried out even for a plurality of gas components.

The method set forth in this invention can also be used for the correction of absorption changes caused by temperature and pressure. A change in temperature alters the weighting of various absorption lines and thus offsets the spectral response of an absorption band. The measuring systems shown in FIGS. 9A, 9B and 10A, 10B make use of no more than two separate measuring lengths, whereby both ducts are provided with exactly the same temperature and pressure. This reduces the disturbing effects of pressure and temperature. Moreover, these methods serve to eliminate some of the temperature sensitivity of individual bandpass filters 9a–9c.

What is claimed is:

1. A sensor device for the non-dispersive analysis of gas mixtures for determining the concentration of one such gas component (Gm) contained therein, whose absorbency may be influenced as a result of collision broadening by other components contained in a gas mixture (GG), said device comprising:

(a) a measuring chamber (5), which contains the gas mixture (GG) to be analyzed, as well as a radiation source (4), which emits through the measuring chamber a radiation (15) over a wavelength range which encompasses an absorption spectral band to be used in the concentration analysis of said gas component;

(b) at least one detector (10 or 14), which is mounted to receive radiation that has passed through the measuring chamber, as well as optical bandpass filters (9a, 9b) positioned between the detector and the radiation source;

(c) separate measuring data channels (1, 2) to which the detector is connected;

(d) an optical gas filter (11), which comprises a filter chamber containing said gas component (Gm), said optical gas filter being located in one of the measuring data channels between one of the detectors (14) and the radiation source (4), whereby from a first measuring data channel (1) is obtained a first signal (S1) based on the radiation passed through the measuring chamber and from a second measuring data channel (2) is obtained a second signal (S2) based on the radiation passed through the measuring chamber and the optical gas filter, wherein;

(e) the measuring chamber (5) and the optical gas filter (11) are in a gas exchange with each other;

(f) the measuring chamber (5) and the optical gas filter (11) are positioned relative to the radiation advancing direction:

whereby beams, which produce the first signal (S1) and the second signal (S2), advance therein over unequal absorption lengths (L1 and respectively L1+L2), and wherein (g) the effective variable amount, expectable during analyses, of an extra gas component (Gm) contained in the optical gas filter (11) is set in a first mixture ($Gm_1$) prior to analyses to have such a value over its absorption length (L2) that:

the second signal (S2) and the first signal (S1) are linearly independent of each other, a mutual relationship of the second signal (S2) and the first signal (S1) is expressible as a cluster of equations (I or II), where the dependence of the first signal (S1) and the second signal (S2) on variables including at least a collision broadening (dT) and a gas component concentration (C), is expressible using coefficients ($A_{ij}$, $B_{ij}$), which are experimentally determined prior to analyses for accurately determining the effect of a collision broadening; and during the analyses of the gas components (GG), at least a concentration (Cf) of the gas component (Gm) to be measured is determined by mathematically solving the variable corresponding to the concentration (Cf) of the gas component (Gm) using the cluster of equations and starting from the signals (S1, S2) obtained as a measuring result (M).

2. A sensor device as set forth in claim 1, characterized in that the device includes one analysis chamber (13a) provided with flow tubes (6, 7) for flowing that gas mixture (GG), a given gas component (Gm) of which is intended to be determined for its concentration during an analysis, that a given length (L1) of this analysis chamber in its extent in the direction of radiation is provided with a mirror (56) which is semi-transmissive or smaller than the beam for deflecting some of the radiation out of this chamber and that this radiation deflected from the measuring chamber (5) is received by the first detector (10), which produces the first signal (S1), as well as the radiation passed through the mirror and the remaining length (L2) of the analysis chamber is received by the second detector (14), which produces the second signal (S2).

3. A sensor device as set forth in claim 2, characterized in that the analysis chamber is provided over some other length (L1+L2) of its extent in the direction of radiation with a semi-transmissive or smaller-than-beam mirror (57) for deflecting some of the radiation out of this chamber and this deflected radiation is received by said second detector (14), which produces the second signal (S2), and that the radiation passed through this second mirror and the remaining length (L3) of the analysis chamber as well as a third optical bandpass filter (9c) is received by a third detector (16), which produces a third signal (S3).

4. A sensor device as set forth in claim 1, characterized in that the device includes one analysis chamber (13b) provided with flow tubes (6, 7) for flowing that gas mixture (GG), a given gas component (Gm) of which is intended to be determined for its concentration during an analysis, as well as additionally a diverting element (54), which is transmissive to the applied radiation without substantial absorption over the applied wavelength band and which is located in the analysis chamber over a portion of the cross-surface of the radiation beam (15) for reducing an absorption length (Lx) of the measuring chamber, the radiation passed through the measuring chamber (5) and this diverting element (54) is received by the first detector (10), which produces the first signal (S1), as well as the radiation passed through the entire length (L1+L2) of the analysis chamber being received by the second detector (14), which produces the second signal (S2).

5. A sensor device as set forth in claim 4, characterized in that the device further includes a second diverting element (55), which is transmissive to the applied radiation without substantial absorption over the applied wavelength band and which is located in the analysis chamber over a portion of the cross-surface of the radiation beam (15) for reducing an absorption length (Lx) of the measuring chamber, the radiation passed through the measuring chamber (5) and this diverting element (55) is received by the second detector (14), which produces the second signal (S2), as well as the radiation passed through the entire length (L1+L2+L3) of the analysis chamber as well as a third optical bandpass filter (9c) being received by a third detector (16), which produces a third signal (S3).

6. A sensor device for the non-dispersive analysis of gas mixtures for determining the concentration of one such gas component (Gm) contained therein, whose absorbency may be influenced as a result of collision broadening by other components contained in a gas mixture (GG), said device comprising:

(a) a measuring chamber (5) which contains the gas mixture (GG) to be analyzed, as well as a radiation source (4), which emits through the measuring chamber a radiation (15) over a wavelength range which encompasses an absorption spectral band to be used in the concentration analysis of said gas component;

(b) at least one detector (10, 14; 20) which is mounted to receive radiation that has passed through the measuring chamber, as well as optical bandpass filters (9a, 9b; 9d) positioned between the detector and the radiation source;

(c) individual measuring data channels (1, 2, 3), to which the detector is connected;

(d) an optical gas filter (11), which comprises a filter chamber containing said gas component (Gm) or a first mixture (Gm$_1$), said optical gas filter being located in one of the measuring ducts between one of the detectors (14), whereby:

from a first measuring data channel (1) is obtained a first signal (S1) based on the radiation passed through the measuring chamber, and from a second measuring data channel (2) is obtained a second signal (S2) based on the radiation passed through the measuring chamber and the optical gas filter, and wherein (e) the measuring chamber (5) is a sealed vessel, which contains said gas component (Gm) or its first mixture (Gm$_1$) in such a fixed effective amount preset by means of a pressure (P2) and/or an absorption length (L2) and/or a concentration (C2) that:

the second signal (S2) and the first signal (S1) are linearly independent of each other, a mutual relationship of the second signal (S2) and the first signal (S1) is expressible as a cluster of equations (I or II), where the dependence of the first signal (S1) and the second signal (S2) on variables including at least a collision broadening (dT) and a gas component concentration (C), is expressible using coefficients ($A_{ij}, B_{ij}$) which are experimentally determined prior to analyses for accurately determining the effect of a collision broadening; and during the analyses of the gas components (GG), at least a concentration (Cf), of the gas component (Gm) to be measured, is determined by mathematically solving the variable corresponding to the concentration (Cf) of the gas component (Gm) using the cluster of equations and starting from the signals (S1, S2) obtained as a measuring result (M).

7. A sensor device as set forth in claim 6, characterized in that the device further includes a second optical gas filter (23), comprising a filter chamber containing said gas component (Gm) or its second mixture (Gm$_2$), that the second gas filter is located in one measuring data channel (3) between a third optical bandpass filter (9c) and a third detector (16), whereby from the third measuring data channel is obtained the third signal (S3) based on the radiation passed through the measuring chamber (5) and the second gas filter.

8. A sensor device as set forth in claim 1, characterized in that the bandpass filters (9a, 9b; 9c; 9d) included between the detectors (10, 14; 16; 20) and the radiation source (4; 24) are as accurately as possible identical with each other or are constituted by various portions or a single portion of one filter and that the transmission bands of the bandpass filters have a width that exceeds one or more widths of an absorption line included in the applied absorption spectral band, but narrower than the distance between the extreme flanks of the applied absorption spectral band.

9. A method for the non-dispersive analysis of gas mixtures for determining the concentration of one such gas component (Gm) contained therein, whose absorbency may be influenced as a result of collision broadening by other components contained in a gas mixture (GG), said method comprising the following steps:

(a) providing a radiation source emitting radiation through the gas mixture to be analyzed over a wavelength range, within which is located an absorption spectral band to be used in the concentration analysis of said gas component;

(b) providing a path of this radiation with an optical first bandpass filter, whose transmission band is aligned with said spectral band, and using a detector for detecting radiation passed through the gas mixture to be analyzed and the optical bandpass filter, this first intensity producing in the detector a first signal (S1);

(c) using said gas component (Gm) or a first mixture (Gm$_1$) thereof placed additionally between the radiation source and the detector for producing in the detector at least one different intensity with a radiation which has also passed through the gas mixture to be analyzed and a second bandpass filter whose transmission band is located within substantially the same wavelength range as the first bandpass filter, this second intensity producing in the detector a second signal (S2), the amount of the second signal producing extra gas component (Gm) selected such that:

the second signal (S2) and the first signal (S1) are linearly independent of each other, a mutual relationship of the second signal (S2) and the first signal (S1) is expressible as a cluster of equations (I or II), where the dependence of the first signal (S1) and the second signal (S2) on variables including at least a collision broadening (dT) and a gas component concentration (C), is expressible using coefficients ($A_{ij}, B_{ij}$), which are experimentally determined prior to analyses for accurately determining the effect of a collision broadening; and (d) determining, during the analyses of the gas components (GG), at least a concentration (Cf) of the gas component (Gm) to be measured, by mathematically solving the variable corresponding to the concentration (Cf) of the gas component (Gm) using the cluster of equations and starting from the signals (S1, S2) obtained as a measuring result (M).

10. The method claim 9, wherein:

coefficients ($A_{ij}, B_{ij}$) of the variables are predetermined prior to analyses by using test gases, whose compositions and the relative collision broadening effects of whose gas components are known; and the information acquired during these steps is stored for use during the analyses.

11. The method of claim 9 wherein the radiation paths producing the first signal (S1) and the second signal (S2) are coupled in parallel and the amount of said extra gas component (Gm) or the fixed amount of extra gas component in the first gas mixture (Gm$_1$) is set prior to analysis to have such a value that the magnitude of the second signal (S2) is 50%–100% of the first signal (S1) within the concentration range of a gas mixture to be analyzed.

12. The method of claim 11 wherein the magnitude of the second signal (S2) is typically within the mid-section of the concentration range and is 70%–90% of the first signal (S1) within the mid-sections of the concentration range of a gas mixture to be analyzed.

13. The method of claim 9 wherein the radiation paths producing the first signal (S1) and the second signal (S2) are coupled in parallel and the amount of said extra gas component (Gm) or the fixed amount of extra gas component in the first gas mixture (Gm$_1$) is set prior to analysis to have such a value that the magnitude of the second signal (S2) is 100%–200% of the first signal (S1) within the concentration range of a gas mixture to be analyzed.

14. The method of claim 13 wherein the magnitude of the second signal (S2) is typically within the mid-section of the concentration range and is 110%–140% of the first signal (S1) within the mid-sections of the concentration range of a gas mixture to be analyzed.

15. The method of claim 9, wherein the radiation paths producing the first signal (S1) and the second signal (S2) are coupled in series, the first gas mixture (Gm) comprising the gas mixture (GG) to be analyzed, and the analyses are preceded by setting:

the absorption length (L2) of the first gas mixture to have such a length that, when in the gas mixture (GG) to be analyzed, the concentration (C) of the gas component (Gm) changes from a bottom limit (Ca) to a top limit (Cb) of a predetermined concentration range, the radiation intensity producing said second signal (S2) decreases merely as a result of the absorption caused by the gas mixture to be analyzed and the extra gas to a value which is no more than about 60% of a value corresponding to the bottom limit; and the absorption length (L1) of the gas mixture to be analyzed to have such a length that, when the concentration of the gas component (Gm) in the gas mixture (GG) to be analyzed is in the middle of a predetermined concentration range, the radiation intensity producing the first signal is 95%–50% of the incoming intensity.

16. The method of claim 15 wherein the radiation intensity producing said second signal (S2) decreases to a value which is no more than approximately 40% of a value corresponding to the bottom limit.

17. The method of claim 16 wherein the second signal (S2) decreases to approximately 30%–5% of a value corresponding to the bottom limit.

18. The method of claim 15 wherein the radiation intensity producing the first signal is approximately 70%–90% of the incoming intensity.

19. The method of claim 9, wherein prior to analyses it further comprises the steps of:

using the gas component (Gm) or a second mixture (Gm$_2$) thereof placed additionally between the radiation source and the detector for producing in the detector a third different intensity with a radiation that has passed through the gas mixture (GG) to be analyzed and a third bandpass filter whose transmission band is located within substantially the same wavelength range as the first and second bandpass filter, this third intensity producing in the detector a third signal (S3);

setting the absorption length (L1 and/or L2 and/or L3) of an extra gas component producing the third signal to have such a value that the magnitude of the third signal (S3) is substantially independent of the concentration of the gas component (Gm) to be examined in the gas mixture (GG) to be analyzed, and that this third signal is taken into account when compiling the concentration measuring result (M) for extra accuracy in the concentration to be measured.

20. The method of claim 9, wherein prior to analyses it further comprises the steps of:

using the gas component (Gm) or a second mixture (Gm$_2$) thereof placed additionally between the radiation source and the detector for producing in the detector a third different intensity with a radiation that has passed through the gas mixture (GG) to be analyzed and a third bandpass filter whose transmission band is located within substantially the same wavelength range as the first and second bandpass filter, this third intensity producing in the detector a third signal;

setting the absorption length (L1 and/or L2 and/or L3) of an extra gas component producing the third signal to have such a value that the magnitude of the third signal (S3) is substantially unequal to the first and second signal (S1 or S2), and that this third signal is taken into account when compiling the concentration measuring result (M) for extra accuracy in the concentration to be measured.

21. The method of claim 9 wherein the transmission bands of at the bandpass filters are adapted to have a width that exceeds at least one width of an absorption line included in the applied absorption spectral band and is narrower than the total width of the applied absorption spectral band, and that said optical bandpass filters are all constituted by a single individual filter and the beams which produce the various signals (S1, S2) pass through the same section of the bandpass filter.

22. The method of claim 10, wherein the analyses are accompanied by implementing the following steps of:

measuring two linearly independent signals (S1, S2);

determining first, primarily by means of the first signal (S1), an approximate concentration (C1) of the gas component (Gm) to be examined in the gas mixture (GG) to be analyzed;

selecting the coefficients of a Jacobian matrix (J) or its inverted matrix determined relative to a collision broadening as starting values for calculating the concentration measuring result (M) by means of that test gas mixture or those test gas mixtures which in terms of composition thereof most closely correspond to the obtained approximate concentration (C1);

introducing into the calculation the obtained second signal (S2) for determining at least the effect of a collision broadening; and performing the calculation of a final concentration (Cf) by interpolating from said approximate values or by iterating from said approximate value or by carrying out both these calculation procedures.

23. The method of claim 10, wherein the analyses are accompanied by implementing the following steps of:

measuring three linearly independent signals (S1, S2, S3);

determining first, primarily by means of the first signal (S1), an approximate concentration (C1) of the gas component (Gm) to be examined in the gas mixture (GG) to be analyzed;

selecting the coefficients of a Jacobian matrix (J) or its inverted matrix determined relative to a collision broadening as starting values for calculating the concentration measuring result (M) by means of that test gas mixture or those test gas mixtures which in terms of composition thereof most closely correspond to the obtained approximate concentration (C1);

introducing into the calculation the obtained second signal (S2) for determining at least the effect of a collision broadening; and performing the calculation of a final concentration (Cf) by interpolating from said approximate values or by iterating from said approximate value or by carrying out both these calculation procedures.

24. The method of claim 10 wherein, during the analyses, other disturbing factors are eliminated by means of the second signal (S2) and that said calculation of the final concentration is implemented by working out the same cluster of equations (I, II or V), whose coefficients ($A_{ij}$, $B_{ij}$) are predetermined prior to the analyses by means of test gas mixtures (Gt).

25. The method of claim 19 wherein during the analyses, other disturbing factors are eliminated by means of the third signal (S3) and that said calculation of the final concentration is implemented by working out the same cluster of equations (I, II, or V), whose coefficients ($A_{ij}$, $B_{ij}$) are predetermined prior to analyses by means of test gas mixtures (Gt).

26. The method of claim 19 wherein:

the first gas mixture ($Gm_1$) producing the second signal (S2) comprises prior to analyses a given test gas mixture (Gt) or a deficit thereof and during analyses a given gas mixture (GG) to be analyzed or a deficit thereof, and that the second mixture ($Gm_2$) producing the third signal (S3) comprises prior to analyses a preset mixture of the gas component (Gm) or a pure gas component (Gm) or alternatively, a test gas mixture (Gt) or a deficit thereof or during analyses the same preset mixture of the gas component (Gm) or alternatively the gas mixture (GG) to be analyzed or a deficit thereof.

27. The method of claim 19 wherein:

the first gas mixture ($Gm_1$) producing the second signal (S2) comprises prior to analyses a given test gas mixture (Gt) and during analyses a given gas mixture (GG) to be analyzed, and that the second mixture ($Gm_2$) producing the third signal (S3) comprises prior to analyses a preset mixture of the gas component (Gm) or a pure gas component (Gm) or alternatively, a test gas mixture (Gt) or a deficit thereof or during analyses the same preset mixture of the gas component (Gm) or alternatively the gas mixture (GG) to be analyzed or a deficit thereof.

28. The method of claim 19 wherein the calculation of the concentration measuring result (M) of the gas component (Gm) included in the gas mixture (GG) to be analyzed is effected by using, depending on its concentration, just any two signals (S1, S2 or S1, S3 or S2, S3) of the three available signals as an effective first signal (S1, S1') and respectively as an effective second signal (S2, S2') and that use is typically made of the signals (S1 and S2) of detectors located closer to a radiation source when the gas component concentration (Gm) is high and the signals (S1'=S2 and S2'=S3) of detectors further way from a radiation source when the gas component concentration (Gm) is low.

29. The method of claim 9 wherein the gas component (Gm), whose concentration is measured, as well as the extra gas component (Gm) comprises carbon dioxide ($CO_2$).

30. The method of claim 9 wherein the analyses are accompanied by measuring the concentration of more than one gas components in the gas mixture (GG), that the number of said second signals (S2) extracted is just one, said second signal being used for calculating the collision broadenings (dT) of all or required gas components to be determined in terms of the concentration thereof and for compiling the concentration measuring results (M) of all gas components to be determined in terms of the concentration thereof.

31. A sensor device for the non-dispersive analysis of gas mixtures for determining the concentration of one such gas component (Gm) contained therein, whose absorbency may be influenced as a result of collision broadening by other components contained in a gas mixture (GG), said device comprising:

(a) a measuring chamber (5) which contains the gas mixture (GG) to be analyzed, as well as a radiation source (4), which emits through the measuring chamber a radiation (15) over a wavelength range which encompasses an absorption spectral band to be used in the concentration analysis of said gas component;

(b) at least one detector (10, 14; 20) which is mounted to receive radiation that has passed through the measuring chamber, as well as optical bandpass filters (9a, 9b; 9d) positioned between the detectors and the radiation source;

(c) said detector being subjected to individual measuring cycles (28, 29, 27);

(d) an optical gas filter (11), which comprises a filter chamber containing said gas component (Gm) or a first mixture ($Gm_1$), said optical gas filter being located between one of the detectors (20) and a radiation source (4) during the measuring cycle, whereby:

from the measuring cycle (28) is obtained a first signal (S1) based on the radiation passed through the measuring chamber, and from the measuring cycle (29) is obtained a second signal (S2) based on the radiation passed through the measuring chamber and the optical gas filter, and wherein (e) the measuring chamber (5) is a sealed vessel, which contains said gas component (Gm) or its first mixture ($Gm_1$) in such a fixed effective amount preset by means of a pressure (P2) and/or an absorption length (L2) and/or a concentration (C2) that:

the second signal (S2) and the first signal (S1) are linearly independent of each other, a mutual relationship of the second signal (S2) and the first signal (S1) is expressible as a cluster of equations (I or II), where the dependence of the first signal (S1) and the second signal (S2) on variables including at least a collision broadening (dT) and a gas component concentration (C), is expressible using coefficients ($A_{ij}$, $B_{ij}$), which are experimentally determined prior to analyses for accurately determining the effect of a collision broadening; and determining, during the analyses of the gas components (GG), at least a concentration (Cf) of the gas component (Gm) to be measured, by mathematically solving the variable corresponding to the concentration (Cf) of the gas component (Gm) using the cluster of equations and starting from the signals (S1, S2) obtained as a measuring result (M).

32. The sensor device of claim 31, characterized in that the device further includes a second optical gas filter (23), comprising a filter chamber containing said gas component (Gm) or its second mixture ($Gm_2$), that the second gas filter is located during one measuring cycle (27) between the detector (20) and the optical bandpass filter (9d) and the radiation source (4), whereby from the third measuring data channel is obtained the third signal (S3) based on the radiation passed through the measuring chamber (5) and the second gas filter.

33. The sensor device of claim 31, characterized in that the bandpass filters (9a, 9b; 9c; 9d) included between the detectors (10, 14; 16; 20) and the radiation source (4; 24) are as accurately as possible identical with each other or are constituted by various portions or a single portion of one filter and that the transmission bands of the bandpass filters have width that exceeds one or more widths of an absorption line included in the applied absorption spectral band, but narrower than the distance between the extreme flanks of the applied absorption spectral band.

34. The sensor device of claim 1 wherein the measuring chamber and the optical gas filter are positioned successively and the beams which produce the first signal and the second signal advance therein in series.

35. The sensor device of claim 1 wherein the measuring chamber and the optical gas filter are positioned side-by-side and the beams that produce the first signal and the second signal travel therein in parallel.

* * * * *